United States Patent
Peterson et al.

(10) Patent No.: US 7,572,918 B2
(45) Date of Patent: Aug. 11, 2009

(54) PROCESS FOR PREPARING SUBSTITUTED 4-AMINO-1-(PYRIDYLMETHYL)PIPERIDINE AND RELATED COMPOUNDS

(75) Inventors: Matthew J Peterson, Redwood City, CA (US); Junning Lee, El Granada, CA (US); Richard J Lee, Foster City, CA (US); Weijiang Zhang, Concord, CA (US)

(73) Assignee: Theravance, Inc., South San Francisco, CA (US)

( * ) Notice: Subject to any disclaimer, the term of this patent is extended or adjusted under 35 U.S.C. 154(b) by 631 days.

(21) Appl. No.: 11/259,833

(22) Filed: Oct. 27, 2005

(65) Prior Publication Data

US 2006/0094878 A1 May 4, 2006

Related U.S. Application Data

(60) Provisional application No. 60/622,915, filed on Oct. 28, 2004.

(51) Int. Cl.
C07D 211/30 (2006.01)
C07D 211/32 (2006.01)
C07D 211/00 (2006.01)
(52) U.S. Cl. .................. 546/186; 546/187; 546/190; 546/194
(58) Field of Classification Search ............... 546/186, 546/194, 187, 190
See application file for complete search history.

(56) References Cited

U.S. PATENT DOCUMENTS

| 7,285,564 | B2 * | 10/2007 | Mammen et al. | 514/318 |
| 7,368,463 | B2 * | 5/2008 | Mammen et al. | 514/326 |
| 2004/0122014 | A1 | 6/2004 | Mammen et al. | |
| 2005/0026954 | A1 | 2/2005 | Mammen et al. | |

FOREIGN PATENT DOCUMENTS

| WO | WO 2004/041806 A2 | 5/2004 |
| WO | WO 2005/007645 A1 | 1/2005 |
| WO | WO 2005/042514 A2 | 5/2005 |

OTHER PUBLICATIONS

Wermuth "The practice of medicinal chemistry" (1996) p. 203-213.*
Berge et al. "Pharmaceutical salts" J. Pharm. sciences, vl. 66, p. 1-2 (1977).*
Pratesi et al. "Affinity and intrinsic . . . " CA 70:37081 (1969).*
CA 60:74793 (1964), see marked entry.*
Laeckmann et al. "Synthesis and biological . . . " Bioorg. med. Chem. v. 10 (2002) p. 1793-1804.*

* cited by examiner

*Primary Examiner*—Janet L. Andres
*Assistant Examiner*—Raymond Covington
(74) *Attorney, Agent, or Firm*—Jeffrey A. Hagenah

(57) ABSTRACT

Processes and intermediates for preparing substituted 4-amino-1-(pyridylmethyl)-piperidine and related compounds in high yield and high purity are described. The substituted 4-amino-1-(pyridylmethyl)piperidine and related compounds prepared by the described processes are useful as muscarinic receptor antagonists.

46 Claims, No Drawings

US 7,572,918 B2

PROCESS FOR PREPARING SUBSTITUTED 4-AMINO-1-(PYRIDYLMETHYL)PIPERIDINE AND RELATED COMPOUNDS

CROSS-REFERENCE TO RELATED APPLICATIONS

This application claims the benefit of U.S. Provisional Application No. 60/622,915, filed on Oct. 28, 2004; the entire disclosure of which is incorporated herein by reference in its entirety.

BACKGROUND OF THE INVENTION

1. Field of the Invention

This invention relates to processes and intermediates for preparing substituted 4-amino-1-(pyridylmethyl)piperidine and related compounds. The compounds prepared by the processes of this invention are useful as muscarinic receptor antagonists.

2. State of the Art

Substituted 4-amino-1-(pyridylmethyl)piperidine and related compounds are disclosed as muscarinic receptor antagonists in WO 2004/041806 A2, published on May 21, 2004; and U.S. patent application Publication No. 2004/0122014, published on Jun. 24, 2004. Such compounds are expected to be useful as therapeutic agents for treating disease conditions mediated by muscarinic receptors, such as overactive bladder. Although methods for preparing such compounds have been described, a need exists for novel processes that provide such compounds in high yield and high purity without the need for isolation of intermediates and chromatographic purification.

SUMMARY OF THE INVENTION

The present invention provides novel processes for preparing substituted 4-amino-1-(pyridylmethyl)piperidine and related compounds. Among other advantages, the present process provides substituted 4-amino-1-(pyridylmethyl)piperidine and related compounds in high yield and high purity without the need for isolation of intermediates and chromatographic purification. Also provided herein are novel intermediates useful for preparing substituted 4-amino-1-(pyridylmethyl)-piperidine and related compounds.

Accordingly, in one of its method aspects, the present invention is directed to a general process for preparing a compound of Formula (I) or a salt or stereoisomer thereof:

wherein the process comprises the steps of:

(a) reacting a compound of Formula (II);

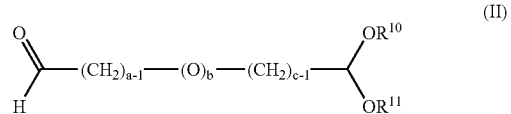

with a compound of Formula (III) or a salt thereof;

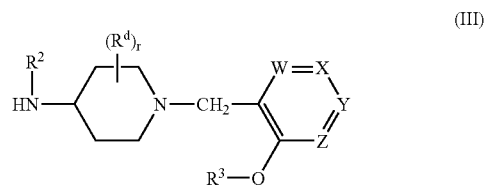

and a first reductant to form a compound of Formula (IV) or a salt thereof;

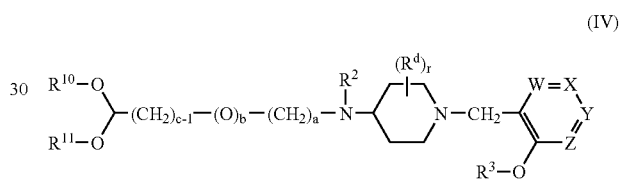

(b) reacting the compound of Formula (IV) or a salt thereof with an acid and water to form a compound of Formula (V) or a salt thereof;

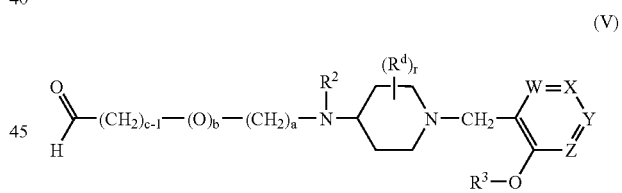

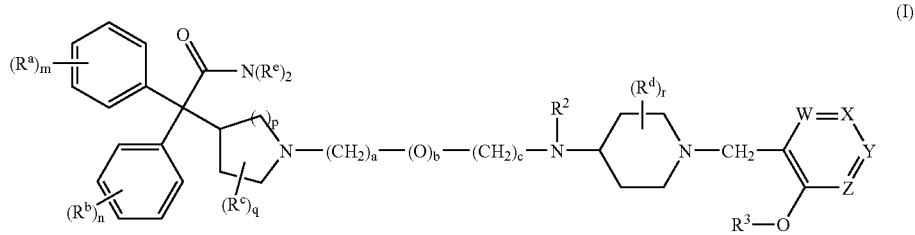

(c) reacting the compound of Formula (V) or a salt thereof; with a compound of Formula (VI) or a salt or stereoisomer thereof;

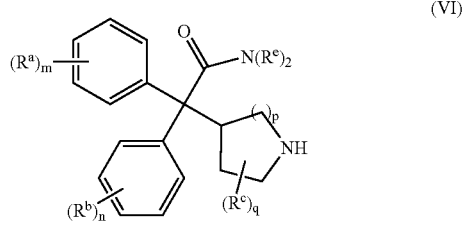

and a second reductant to form the compound of Formula (I) or a salt or stereoisomer thereof;
wherein
W, X, Y and Z are independently selected from the group consisting of CH, $CR^4$, N and N→O; provided that at least one and no more than two of W, X, Y and Z are N or N→O;

$R^2$ is selected from the group consisting of hydrogen, $C_{1-6}$ alkyl, $C_{2-6}$ alkenyl, $C_{2-6}$ alkynyl, $C_{3-6}$ cycloalkyl, —$CH_2$—$R^5$ and —$(CH_2)_x$—$R^6$; wherein each alkyl, alkenyl, alkynyl and cycloalkyl group is optionally substituted with 1 to 5 fluoro substituents;

each $R^3$ is independently selected from the group consisting of hydrogen, $C_{1-6}$ alkyl, $C_{2-6}$ alkenyl, $C_{2-6}$ alkynyl, $C_{3-6}$ cycloalkyl, —$CH_2$—$R^7$ and —$(CH_2)_y$—$R^8$ wherein each alkyl, alkenyl, alkynyl and cycloalkyl group is optionally substituted with 1 to 5 fluoro substituents;

each $R^4$ is independently selected from the group consisting of $C_{1-6}$ alkyl, $C_{2-6}$ alkenyl, $C_{2-6}$ alkynyl, $C_{3-6}$ cycloalkyl, —$OR^3$ and halo or two adjacent $R^4$ groups are joined to form $C_{3-6}$ alkylene, —O—$(C_{2-4}$ alkylene)-, —O—$(C_{1-4}$ alkylene)-O—, —(O)C—CH=CH— or —CH=CH—C(O)— or when Z is $CR^4$, —$OR^3$ and $R^4$ are joined to form —O—$(C_{2-5}$ alkylene)- or —O—$(C_{1-5}$ alkylene)-O— wherein each alkyl, alkylene, alkenyl, alkynyl and cycloalkyl group is optionally substituted with 1 to 5 fluoro substituents;

each $R^5$ and $R^7$ is independently selected from the group consisting of $C_{3-5}$ cycloalkyl, $C_{6-10}$ aryl, —C(O)($C_{6-10}$ aryl), $C_{2-9}$ heteroaryl, —C(O)($C_{2-9}$ heteroaryl) and $C_{3-6}$ heterocyclic wherein the cycloalkyl group is optionally substituted with 1 to 5 fluoro substituents and the aryl, heteroaryl and heterocyclic groups are optionally substituted with 1 to 3 substituents independently selected from $R^k$ and the aryl and heteroaryl groups are optionally further substituted with a phenyl group, where the phenyl group is optionally substituted with 1 to 3 substituents independently selected from $R^k$;

each $R^6$ and $R^8$ is independently selected from the group consisting of —OH, —$OR^9$, —$SR^9$, —$S(O)R^9$, —$S(O)_2R^9$, —$C(O)R^9$, $C_{3-5}$ cycloalkyl, $C_{6-10}$ aryl, $C_{2-9}$ heteroaryl and $C_{3-6}$ heterocyclic wherein the cycloalkyl group is optionally substituted with 1 to 5 fluoro substituents; and the aryl, heteroaryl and heterocyclic groups are optionally substituted with 1 to 3 substituents independently selected from $R^k$;

each $R^9$ is independently selected from the group consisting of $C_{1-4}$ alkyl, $C_{3-5}$ cycloalkyl, $C_{6-10}$ aryl and $C_{2-9}$ heteroaryl wherein the alkyl and cycloalkyl groups are optionally substituted with 1 to 5 fluoro substituents; and the aryl and heteroaryl groups are optionally substituted with 1 to 3 substituents independently selected from $R^k$;

$R^{10}$ and $R^{11}$ are independently $C_{1-6}$ alkyl; or $R^{10}$ and $R^{11}$ are joined to form $C_{2-6}$ alkylene;

each $R^a$ and $R^b$ is independently selected from the group consisting of $C_{1-4}$ alkyl, $C_{2-4}$ alkenyl, $C_{2-4}$ alkynyl, $C_{3-6}$ cycloalkyl, cyano, halo, —$OR^f$, —$SR^f$, —$S(O)R^f$, —$S(O)_2R^f$ and —$NR^gR^h$; or two adjacent $R^a$ groups or two adjacent $R^b$ groups are joined to form $C_{3-6}$ alkylene, —$(C_{2-4}$ alkylene)-O— or —O—$(C_{1-4}$ alkylene)-O— wherein each alkyl, alkylene, alkenyl, alkynyl and cycloalkyl group is optionally substituted with 1 to 5 fluoro substituents;

each $R^c$ and $R^d$ is independently selected from the group consisting of $C_{1-4}$ alkyl and fluoro wherein each alkyl group is optionally substituted with 1 to 5 fluoro substituents;

each $R^e$ is independently selected from the group consisting of hydrogen, $C_{1-6}$ alkyl, $C_{2-6}$ alkenyl, $C_{2-6}$ alkynyl, $C_{3-6}$ cycloalkyl, $C_{6-10}$ aryl, $C_{2-9}$ heteroaryl, $C_{3-6}$ heterocyclic, —$CH_2$—$R^i$ and —$CH_2CH_2$—$R^j$ or both $R^e$ groups are joined together with the nitrogen atom to which they are attached to form $C_{3-6}$ heterocyclic; wherein each alkyl, alkenyl, alkynyl and cycloalkyl group is optionally substituted with 1 to 5 fluoro substituents; and each aryl, heteroaryl and heterocyclic group is optionally substituted with 1 to 3 substituents independently selected from $R^k$;

each $R^f$ is independently selected from the group consisting hydrogen, $C_{1-4}$ alkyl, $C_{2-4}$ alkenyl, $C_{2-4}$ alkynyl and $C_{3-6}$ cycloalkyl wherein each alkyl, alkenyl, alkynyl and cycloalkyl group is optionally substituted with 1 to 5 fluoro substituents;

each $R^g$ and $R^h$ is independently selected from the group consisting of hydrogen, $C_{1-4}$ alkyl, $C_{2-4}$ alkenyl, $C_{2-4}$ alkynyl and $C_{3-6}$ cycloalkyl or $R^g$ and $R^h$ are joined together with the nitrogen atom to which they are attached to form $C_{3-6}$ heterocyclic; wherein each alkyl, alkenyl, alkynyl and cycloalkyl group is optionally substituted with 1 to 5 fluoro substituents, and the heterocyclic group is optionally substituted with 1 to 3 substituents independently selected from $C_{1-4}$ alkyl and fluoro;

each $R^i$ is independently selected from the group consisting of $C_{3-6}$ cycloalkyl, $C_{6-10}$ aryl, $C_{2-9}$ heteroaryl and $C_{3-6}$ heterocyclic; wherein aryl, cycloalkyl, heteroaryl and heterocyclic group is optionally substituted with 1 to 3 substituents independently selected from $R^k$;

each $R^j$ is independently selected from the group consisting of $C_{3-6}$ cycloalkyl, $C_{6-10}$ aryl, $C_{2-9}$ heteroaryl, $C_{3-6}$ heterocyclic, —OH, —O($C_{1-6}$ alkyl), —O($C_{3-6}$ cycloalkyl), —O($C_{6-10}$ aryl), —O($C_{2-9}$ heteroaryl), —S($C_{1-6}$ alkyl), —S(O)($C_{1-6}$ alkyl), —$S(O)_2(C_{1-6}$ alkyl), —S($C_{3-6}$ cycloalkyl), —S(O)($C_{3-6}$ cycloalkyl), —$S(O)_2(C_{3-6}$ cycloalkyl), —S($C_{6-10}$ aryl), —S(O)($C_{6-10}$ aryl), —$S(O)_2(C_{6-10}$ aryl), —S($C_{2-9}$ heteroaryl), —S(O)($C_{2-9}$ heteroaryl) and —$S(O)_2(C_{2-9}$ heteroaryl) wherein each alkyl group is optionally substituted with 1 to 5 fluoro substituents and each aryl, cycloalkyl, heteroaryl and heterocyclic group is optionally substituted with 1 to 3 substituents independently selected from $R^k$;

each $R^k$ is independently selected from the group consisting of $C_{1-4}$ alkyl, $C_{2-4}$ alkenyl, $C_{2-4}$ alkynyl, cyano, halo, —$OR^f$, —$SR^f$, —$S(O)R^f$, —$S(O)_2R^f$ and —$NR^gR^h$ or two adjacent $R^k$ groups are joined to form $C_{3-6}$ alkylene, —$(C_{2-4}$ alkylene)-O— or —O—$(C_{1-4}$ alkylene)-O— wherein each alkyl, alkylene, alkenyl and alkynyl group is optionally substituted with 1 to 5 fluoro substituents;

each —$CH_2$— group in a compound of Formula (I) is optionally substituted with one or two substituents independently selected from the group consisting of $C_{1-2}$ alkyl, fluoro where each alkyl group is optionally substituted with 1 to 3 fluoro groups;

a is an integer from 2 to 7;
b is 0 or 1;
c is an integer from 2 to 7; provided that a+b+c equals 7, 8 or 9;

m is an integer from 0 to 3;
n is an integer from 0 to 3;
p is 1 or 2;
q is an integer from 0 to 4;
r is an integer from 0 to 4;
x is an integer from 2 to 4; and
y is an integer from 2 to 4.

In one embodiment of the invention, the process further comprises:

(d) forming an aqueous solution comprising a hydrogen addition salt of the compound of Formula (I);

(e) contacting the aqueous solution from step (d) with a water-immiscible organic diluent; and then (f) separating the water-immiscible organic diluent from the aqueous solution.

In another embodiment of the invention, the process further comprises:

(g) forming a water-immiscible organic diluent solution comprising the compound of Formula (I) and a water-immiscible organic diluent;

(h) contacting the water-immiscible organic diluent solution from step (g) with an aqueous solution comprising an alkali metal carbonate and an alkali metal metabisulfite; and then (i) separating the water-immiscible organic diluent solution from the aqueous solution.

In yet another embodiment, the process further comprises (j) contacting the compound of Formula (I) with napthalene-1,5-disulfonic acid to form a napthalene-1,5-disulfonic acid salt of the compound of Formula (I).

The present invention also provides intermediates that are useful in processes for preparing compounds of Formula (I). Accordingly, in one of its composition aspects, the present invention is directed to a compound of Formula (IV)

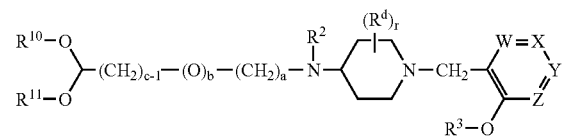

or a salt or stereoisomer thereof; wherein

W, X, Y, Z, $R^2$, $R^3$, $R^4$, $R^5$, $R^6$, $R^7$, $R^8$, $R^9$, $R^{10}$, $R^{11}$, $R^d$, $R^k$, $R^f$, $R^g$, $R^h$, a, b, c, r, x and y are as defined herein.

In another of its composition aspects, this invention is directed to a compound of Formula (XI):

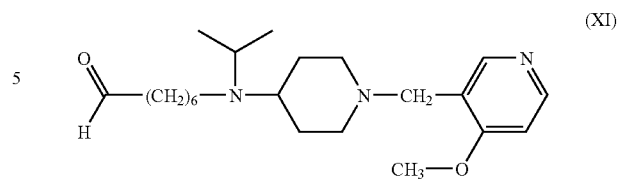

or a salt thereof.

DETAILED DESCRIPTION OF THE INVENTION

This invention provides novel processes for preparing substituted 4-amino-1-(pyridylmethyl)-piperidine and related compounds of Formula (I) or Formula (XII) or salts or solvates or stereoisomers thereof. The compounds of Formulae (I)-(XII) may contain one or more chiral centers and, when such a chiral center or centers are present, the invention includes racemic mixtures, pure stereoisomers (i.e., individual enantiomers or diastereomers) and stereoisomer-enriched mixtures of such isomers, unless otherwise indicated. When a particular stereoisomer is shown, it will be understood by those skilled in the art that minor amounts of other stereoisomers may be present unless otherwise indicated, provided that utility as a whole is not eliminated by the presence of such other isomers.

The compounds of Formulae (I)-(XII) may also contain several basic groups (e.g., amino groups) and therefore, the compounds of Formulae (I)-(XII) can exist in various salt forms. All such salt forms are included within the scope of this invention. Also, included within the scope of this invention are pharmaceutically-acceptable solvates of the compounds of Formulae (I)-(XII) or the salts thereof.

Additionally, all cis-trans or E/Z isomers (geometric isomers) and tautomeric forms of the compounds of Formula (I) are within the scope of this invention. For example, when $R^3$ is hydrogen and X is N, then such compounds may exist in the pyridin-4-one form.

The compounds of Formulae (I)-(XII) may also include isotopically-labeled compounds, i.e., where one or more atoms have been enriched with atoms having an atomic mass different from the atomic mass found predominately in nature. Examples of isotopes that may be incorporated into the compounds of Formula (I) include, but are not limited to, $^2H$, $^3H$, $^{13}C$, $^{14}C$, $^{15}N$, $^{18}O$ and $^{17}O$.

The nomenclature used to describe the compounds of Formula (I) is illustrated by the following representative example. The name 4-{N-[7-(3-(S)-1-carbamoyl-1,1-diphenylmethyl)pyrrolidin-1-yl]hept-1-yl]-N-(ethyl)amino}-1-(4-methoxypyrid-3-ylmethyl)piperidine designates a compound of the formula:

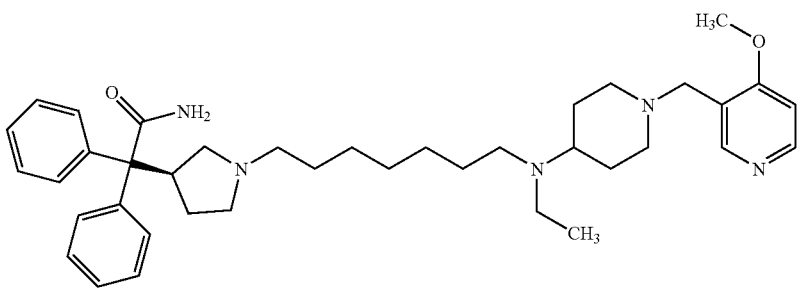

This compound can also be named using AutoNom (MDL, San Leandro Calif.) as follows: 2-[(S)-1-(7-{ethyl-[1-(4-methoxypyridin-3-ylmethyl)piperidin-4-yl]amino}heptyl)pyrrolidin-3-yl}-2,2-diphenylacetamide.

Definitions

When describing the compounds and processes of this invention, the following terms have the following meanings unless otherwise indicated.

The term "alkyl" refers to a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" refers to a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkenyl" refers to a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like.

The term "alkynyl" refers to a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like.

The term "aryl" refers to a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "cycloalkyl" refers to a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like.

The term "halo" refers to fluoro, chloro, bromo and iodo.

The term "heteroaryl" refers to a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heterocyclyl" or "heterocyclic" refers to a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring carbon atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom.

The term "(4-methoxypyrid-3-yl)methyl" refers to a group of the formula:

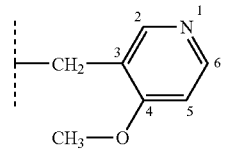

Related pyridyl groups are named in a similar manner.

The term "pyridine N-oxide" refers to a pyridine compound in which the nitrogen atom of the pyridine has been oxidized, i.e., $N^+\!\!-\!\!O^-$ or $N\rightarrow O$.

The term "pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids. Salts derived from pharmaceutically-acceptable inorganic bases include ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically-acceptable acids include acetic, ascorbic, benzenesulfonic, benzoic, camphosulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic, xinafoic and the like. Particularly preferred are citric, hydrobromic, hydrochloric, isethionic, maleic, phosphoric, sulfuric and tartaric acids.

The term "salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient. The term "hydrogen addition salt of a compound of Formula (I)" refers to a salt of a compound of Formula (I) in which one or more of the basic nitrogen atoms in the compound of Formula (I) have been protonated with an acid to form a salt.

The term "solvate" refers to a complex or aggregate formed by one or more molecules of a solute, i.e. a compound of formula I or a pharmaceutically-acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "leaving group" refers to a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected derivatives thereof" refers to a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, N.Y., 1999, and references cited therein.

The term "amino-protecting group" refers to a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term "carboxy-protecting group" refers to a protecting group suitable for preventing undesired reactions at a carboxy group. Representative carboxy-protecting groups include, but are not limited to, esters, such as methyl, ethyl, tert-butyl, benzyl (Bn), p-methoxybenzyl (PMB), 9-fluroenylmethyl (Fm), trimethylsilyl (TMS), tert-butyldimethylsilyl (TBS), diphenylmethyl (benzhydryl, DPM) and the like.

Representative and Illustrative Embodiments

The following substituents and values are intended to provide representative or illustrative examples of various aspects and embodiments of this invention. These representative values are intended to further define such aspects and embodiments and are not intended to exclude other embodiments or limit the scope of the invention unless specifically indicated. In this regard, the representation that a particular value or substitutent is preferred is not intended in any way to exclude other values or substituents from this invention unless specifically indicated.

In certain embodiments, b is 0, and a and c are as defined herein. In other embodiments, b is 1, and a and c are as defined herein.

In certain embodiments, $-(CH_2)_a-(O)_b-(CH_2)_c-$ is $-(CH_2)_7-$, $-(CH_2)_8-$, $-(CH_2)_9-$, $-(CH_2)_2-O-(CH_2)_4-$, $-(CH_2)_2-O-(CH_2)_5-$, $-(CH_2)_2-O-(CH_2)_6-$, $-(CH_2)_3-O-(CH_2)_3-$, $-(CH_2)_3-O-(CH_2)_4-$, $-(CH_2)_3-O-(CH_2)_5-$, $-(CH_2)_4-O-(CH_2)_2-$, $-(CH_2)_4-O-(CH_2)_3-$, $-(CH_2)_4-O-(CH_2)_4-$, $-(CH_2)_5-O-(CH_2)_2-$, $-(CH_2)_5-O-(CH_2)_3-$ or $-(CH_2)_6-O-(CH_2)_2-$.

In other embodiments, $-(CH_2)_a-(O)_b-(CH_2)_c-$ is $-(CH_2)_7-$, $-(CH_2)_8-$, $-(CH_2)_9-$, $-(CH_2)_3-O-(CH_2)_3-$ or $-(CH_2)_4-O-(CH_2)_4-$. In still other embodiments, $-(CH_2)_a-(O)_b-(CH_2)_c-$ is $-(CH_2)_7-$.

In $-(CH_2)_a-(O)_b-(CH_2)_c-$ each $-CH_2-$ group is optionally substituted with 1 or 2 substituents selected from the group consisting of methyl, ethyl and fluoro, wherein the methyl and ethyl groups are optionally substituted with 1 to 3 fluoro substituents. Representative substituents include fluoro, methyl, fluoromethyl, difluoromethyl, trifluoromethyl, 2,2,2-trifluoroethyl and the like.

In certain embodiments, $R^2$ is $C_{1-4}$ alkyl. Preferably, $R^2$ is $C_{2-3}$ alkyl wherein the alkyl group is optionally substituted with 1 to 3 fluoro substituents, more preferably, $R^2$ is methyl, ethyl, n-propyl, isopropyl, n-butyl and isobutyl, even more preferably, $R^2$ is ethyl, n-propyl and isopropyl.

In other embodiments, $R^2$ is $-CH_2-R^5$, wherein $R^5$ is as defined herein. In these embodiments, $R^2$ (i.e., $-CH_2-R^5$) is preferably selected from the group consisting of:

(a) $-CH_2-(C_{3-5}$ cycloalkyl); and more preferably, $-CH_2-(C_3$ cycloalkyl); wherein the cycloalkyl group is optionally substituted with 1 to 3 fluoro substituents;

(b) $-CH_2$-(phenyl), i.e., benzyl, wherein the phenyl group is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, $-O(C_{1-4}$ alkyl), $-S(C_{1-4}$ alkyl) and $-S(O)_2(C_{1-4}$ alkyl); where each alkyl group is optionally substituted with 1 to 3 fluoro substituents;

(c) $-CH_2$-(naphthyl); wherein the naphthyl group (i.e., a 1- or 2-naphthyl group) is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, $-O(C_{1-4}$ alkyl), $-S(C_{1-4}$ alkyl) and $-S(O)_2(C_{1-4}$ alkyl); where each alkyl group is optionally substituted with 1 to 3 fluoro substituents;

(d) $-CH_2$-(biphenyl), wherein each phenyl ring of the biphenyl group (i.e., a 1,2-, 1,3- or 1,4-biphenyl group) is optionally substituted with 1 to 3 substituents independently selected from $R^k$; preferably, 1 or 2 substituents (preferably 1 substituent) selected from the group consisting of $C_{1-4}$ alkyl, cyano, fluoro, chloro, $-O(C_{1-4}$ alkyl), $-S(C_{1-4}$ alkyl) and $-S(O)_2(C_{1-4}$ alkyl); where each alkyl group is optionally substituted with 1 to 3 fluoro substituents;

(e) $-CH_2$-(pyridyl); wherein the pyridyl group (i.e., a 2-, 3- or 4-pyridyl group) is optionally substituted with 1 to 3 substituents independently selected from $R^k$, preferably, 1 or 2 substituents (preferably, 1 substituent) selected from the group consisting of $C_{1-4}$ alkyl, cyano, fluoro, chloro, $-O(C_{1-4}$ alkyl), $-S(C_{1-4}$ alkyl) and $-S(O)_2(C_{1-4}$ alkyl) where each alkyl group is optionally substituted with 1 to 3 fluoro substituents; and (f) $-CH_2C(O)$-(phenyl), i.e., phenacyl, wherein the phenyl ring of the phenacyl group is optionally substituted with 1 to 3 substituents independently selected from $R^k$, preferably, 1 or 2 substituents (preferably, 1 substituent) selected from the group consisting of $C_{1-4}$ alkyl, cyano, fluoro, chloro, $-O(C_{1-4}$ alkyl), $-S(C_{1-4}$ alkyl) and $-S(O)_2(C_{1-4}$ alkyl) where each alkyl group is optionally substituted with 1 to 3 fluoro substituents.

Representative $R^2$ groups in these embodiments include cyclopropylmethyl, cyclobutylmethyl and cyclopentylmethyl, benzyl, 4-cyanobenzyl, 4-methylbenzyl, 4-trifluoromethoxybenzyl, 4-difluoromethoxybenzyl, 4-thiomethoxybenzyl, 4-methanesulfonylbenzyl, 4-tert-butylbenzyl, 4-phenylbenzyl, pyridyl-2-ylmethyl, pyrid-3-ylmethyl, napthth-2-ylmethyl, 3-cyanophenacyl, and 3,4-ethylenedioxyphenacyl.

In yet another embodiment, $R^2$ is —$(CH_2)_x$—$R^6$, wherein x is 2, 3 or 4, preferably, 2 or 3. In this embodiment, $R^2$ (i.e., —$(CH_2)_x$—$R^6$) is preferably selected from the group consisting of:

(a) —$(CH_2)_x$—OH;
(b) —$(CH_2)_x$—O($C_{1-4}$ alkyl), more preferably, —$(CH_2)_x$—O($C_{1-3}$ alkyl) and still more preferably, —$(CH_2)_x$—O($C_{1-2}$ alkyl) wherein the alkyl group is optionally substituted with 1 to 3 fluoro substituents;
(c) —$(CH_2)_x$—S($C_{1-4}$ alkyl), —$(CH_2)_x$—S(O)($C_{1-4}$ alkyl), or —$(CH_2)_x$—S(O)$_2$($C_{1-4}$ alkyl) more preferably, —$(CH_2)_x$—S($C_{1-3}$ alkyl), —$(CH_2)$,—S(O)($C_{1-3}$ alkyl), or —$(CH_2)_x$—S(O)$_2$($C_{1-3}$ alkyl) and still more preferably, —$(CH_2)_x$—S($C_{1-2}$ alkyl), —$(CH_2)_x$—S(O)($C_{1-2}$ alkyl), or —$(CH_2)_x$—S(O)$_2$($C_{1-2}$ alkyl) wherein the alkyl group is optionally substituted with 1 to 3 fluoro substituents;
(d) —$(CH_2)_x$-(phenyl), e.g., phenethyl, wherein the phenyl group is optionally substituted with 1 to 3 substituents independently selected from $R^k$, preferably, 1 or 2 substituents (preferably, 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl) where each alkyl group is optionally substituted with 1 to 3 fluoro substituents;
(e) —$(CH_2)_x$—(O-phenyl), wherein the phenyl group is optionally substituted with 1 to 3 substituents independently selected from $R^k$ preferably, 1 or 2 substituents (preferably, 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl) where each alkyl group is optionally substituted with 1 to 3 fluoro substituents;
(f) —$(CH_2)_x$-(naphthyl), wherein the naphthyl group (i.e., a 1- or 2-naphthyl group) is optionally substituted with 1 to 3 substituents independently selected from $R^k$, preferably, 1 or 2 substituents (preferably 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl) where each alkyl group is optionally substituted with 1 to 3 fluoro substituents; and
(g) —$(CH_2)_x$-(indolyl), wherein the indolyl group (i.e., a 2- or 3-indolyl group) is optionally substituted with 1 to 3 substituents independently selected from $R^k$ preferably, 1 or 2 substituents (preferably, 1 substituent) selected from the group consisting of $C_{1-4}$ alkyl, cyano, fluoro, chloro, —O($C_{1-4}$ alkyl), —S($C_{1-4}$ alkyl) and —S(O)$_2$($C_{1-4}$ alkyl); where each alkyl group is optionally substituted with 1 to 3 fluoro substituents.

For these embodiments, representative $R^2$ groups include 2-hydroxyethyl, 2-methoxyethyl, 2-(methylthio)ethyl, 2-ethoxyethyl, 2-(ethylthio)ethyl, 2-(2,2,2-trifluoroethoxy)ethyl, 2-phenethyl, 2-(naphth-1-yl)ethyl, 2-(indol-3-yl)ethyl, 3-hydroxypropyl, 3-methoxypropyl, 3-ethoxypropyl, 3-phenylpropyl and 3-phenoxypropyl.

In certain embodiments, $R^2$ is $C_{1-4}$ alkyl, —$CH_2$—($C_{3-5}$ alkyl), —$CH_2$—($C_{3-5}$ cycloalkyl), —$CH_2CH_2$—OH or —$CH_2CH_2$—O($C_{1-4}$ alkyl). Representative $R^2$ groups include ethyl, n-propyl, isopropyl, cyclopropylmethyl or 2-hydroxyethyl.

In certain embodiments, each $R^3$ is independently selected from the group consisting of hydrogen, $C_{1-4}$ alkyl, cyclopropylmethyl and 2-hydroxyethyl wherein each alkyl group is optionally substituted with 1 to 5 fluoro substituents. In other embodiments, each $R^3$ is hydrogen or $C_{1-4}$ alkyl wherein each alkyl group is optionally substituted with 1 to 4 fluoro substituents. In still other embodiments, each $R^3$ is independently $C_{1-3}$ alkyl optionally substituted with 1 to 4 fluoro substituents. In a particular embodiment, each $R^3$ is methyl.

Representative $R^3$ groups include hydrogen, methyl, ethyl, n-propyl, isopropyl, difluoromethyl, trifluoromethyl, 2,2,2-trifluoroethyl, 1,3-difluoroprop-2-yl, 1,1,3,-trifluoroprop-2-yl, and 1,1,3,3-tetrafluoroprop-2-yl.

In certain embodiments, $R^4$ is selected from the group consisting of $C_{1-4}$ alkyl, —$OR^3$ and halo wherein $R^3$ is as defined herein including its preferred embodiments and wherein the alkyl group is optionally substituted with 1 to 5 fluoro substituents. In other embodiments, $R^4$ is $C_{1-3}$ alkyl, —$OR^3$, fluoro and chloro; wherein the alkyl group is optionally substituted with 1 to 3 fluoro substituents. In still other embodiments, $R^4$ is $C_{1-2}$ alkyl, —$OR^3$, fluoro or chloro. In one embodiment, $R^4$ is methyl, —$OR^3$, fluoro or chloro. In preferred embodiments, $R^4$ is —$OR^3$.

In certain embodiments, one or two of W, X, Y and Z are N or N→O. In other embodiments, one and only one of W, X, Y and Z is N or N→O, i.e., the ring containing W, X, Y and Z is a pyridine or pyridine N-oxide ring. In still other embodiments, W, X, Y and Z are defined as follows:

(a) W is N; X is CH; Y is CH; and Z is CH;
(b) W is CH or $CR^4$; X is N; Y is CH and Z is CH;
(c) W is CH or $CR^4$; X is CH; Y is N; and Z is CH;
(d) W is CH or $CR^4$; X is CH; Y is CH; and Z is N; or
(e) W is CH; X is N; Y is CH and Z is CH.

In other embodiments, two of W, X, Y and Z are N or N→O, i.e., the ring containing W, X, Y and Z is a pyridazine, pyrimidine or pyrazine ring or the corresponding N-oxides.

In one embodiment, when W, X, Y and Z are not CH or $CR^4$, they are N.

In another embodiment, when X, Y and Z are not N or N→O, they are CH.

In the compounds of Formula (I), the —$CH_2$— group attached to the piperidine nitrogen atom and the pyridine ring containing W, X, Y and Z, is optionally substituted with 1 or 2 substituents selected from the group consisting of methyl, ethyl and fluoro, wherein the methyl and ethyl groups are optionally substituted with 1 to 3 fluoro substituents. Representative substituents include fluoro, methyl, fluoromethyl, difluoromethyl, trifluoromethyl, 2,2,2-trifluoroethyl and the like.

When present, each $R^a$ or $R^b$ is preferably independently selected from the group consisting of $C_{1-4}$ alkyl, fluoro, chloro and —$OR^f$ wherein each alkyl group is optionally substituted with 1 to 3 fluoro substituents. More preferably, each $R^a$ and $R^b$ is $C_{1-2}$ alkyl or fluoro. Particularly preferred $R^a$ and $R^b$ groups include methyl, ethyl, n-propyl, isopropyl, difluoromethyl, trifluoromethyl, 2,2,2-trifluoroethyl, fluoro, chloro, methoxy, ethoxy, difluoromethoxy and trifluoromethoxy.

When present, each $R^c$ or $R^d$ is preferably independently selected from the group consisting of $C_{1-2}$ alkyl and fluoro wherein each alkyl group is optionally substituted with 1 to 3 fluoro substituents. When two $R^c$ or $R^d$ substituents are present, they can be on the same or different carbon atoms. Particularly preferred $R^c$ and $R^d$ groups include methyl, ethyl, difluoromethyl, trifluromethyl and fluoro.

Preferably, each $R^e$ is independently hydrogen or $C_{1-4}$ alkyl. More preferably, each $R^e$ is independently hydrogen or $C_{1-2}$ alkyl. Still more preferably, each $R^e$ is hydrogen. Particularly preferred $R^e$ groups include hydrogen, methyl and ethyl.

Alternatively, both $R^e$ groups are joined together with the nitrogen atom to which they are attached to form a $C_{5-6}$ heterocyclic ring optionally containing one additional heteroatom selected from nitrogen, oxygen or sulfur. Particularly preferred heterocyclic rings include pyrrolidin-1-yl, piperidin-1-yl, piperazin-1-yl, morpholin-4-yl and thiomorpholin-4-yl.

Preferably, each $R^i$ is independently phenyl wherein each phenyl group is optionally substituted with 1 to 3 substituents independently selected from $R^k$.

Preferably, each $R^j$ is independently selected from the group consisting of phenyl, —OH and —O($C_{1-2}$ alkyl) wherein each alkyl group is optionally substituted with 1 to 3 fluoro substituents and each phenyl group is optionally substituted with 1 to 3 substituents independently selected from $R^k$.

Preferably, m is 0, 1 or 2, more preferably, m is 0 or 1 and still more preferably, m is 0.

Preferably, n is 0, 1 or 2, more preferably, n is 0 or 1 and still more preferably, n is 0.

Preferably, m and n are both 0.

Preferably, p is 1.

When p is 1, i.e., when the ring defined by p is a pyrrolidine ring, then in one embodiment, the stereocenter at the 3-position of the pyrrolidine ring (i.e., the carbon atom bearing the 1-carbamoyl-1,1-diphenylmethyl group) preferably has the (S) stereochemistry. In another embodiment, this stereocenter has the (R) stereochemistry.

Preferably, q is 0.

Preferably, r is 0.

Preferably, q is 0 and r is 0.

Preferably, x is 2 or 3.

Preferably, y is 2 or 3.

In one embodiments, $R^{10}$ and $R^{11}$ are selected independently from $C_{1-3}$ alkyl; or are joined together to form $C_{2-4}$ alkylene. Representative $R^{10}$ and $R^{11}$ groups include methyl, ethyl, n-propyl and isopropyl; or 1,2-ethylene, 1,2-propylene, 1,3-propylene, 2-methyl-1,2-propylene, 2,3-butylene and the like.

In certain embodiments, b, m, n, q and r are 0 and p is 1.

In other embodiments, each $R^e$ is hydrogen, $R^2$ is $C_{1-4}$ alkyl, $R^3$ is $C_{1-4}$ alkyl, b, m, n, q and r are 0, p is 1, W, Y and Z are CH and X is N.

In certain embodiments, —(CH$_2$)$_a$—(O)$_b$—(CH$_2$)$_c$— is —(CH$_2$)$_7$—, —(CH$_2$)$_8$— or —(CH$_2$)$_9$—, $R^3$ is methyl, W is CH, X is N; Y is CH, Z is C,; both $R^e$ are hydrogen, m, n, q and r are 0 p is 1 and $R^2$ is as defined herein including its preferred embodiments.

In other embodiments, —(CH$_2$)$_a$—(O)$_b$—(CH$_2$)$_c$— is —(CH$_2$)$_7$—, —(CH$_2$)$_8$— or —(CH$_2$)$_9$—, $R^3$ is ethyl, W is CH, X is N, Y is CH, Z is CH, both $R^e$ are hydrogen, m, n, q and r are 0, p is 1 and $R^2$ is as defined herein including its preferred embodiments.

In still other embodiments, —(CH$_2$)$_a$—(O)$_b$—(CH$_2$)$_c$— is —(CH$_2$)$_7$—, —(CH$_2$)$_8$— or —(CH$_2$)$_9$— $R^2$ is isopropyl, W is CH, X is N, Y is CH, Z is CH, both $R^e$ are hydrogen; m, n, q and r are 0, p is 1 and $R^3$ is as defined herein including its preferred embodiments.

In still other embodiments, $R^2$ is isopropyl, $R^3$ is methyl, W is CH, X is N, Y is CH, Z is CH, both $R^e$ are hydrogen, m, n, q and r are 0, p is 1, and $R^1$ is as defined herein including its preferred embodiments.

In still other embodiments, $R^2$ is isopropyl, $R^3$ is ethyl, W is CH, X is N, Y is CH, Z is CH, both $R^e$ are hydrogen, m, n, q and r are 0, p is 1 and $R^1$ is as defined herein including its preferred embodiments.

Other embodiments include compounds of formula (XII):

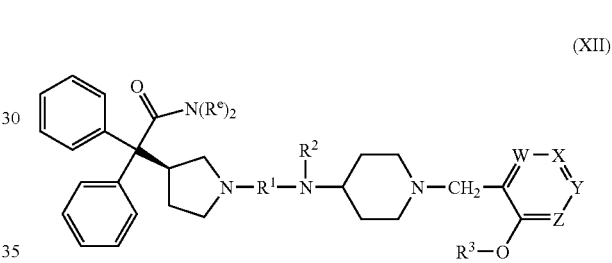

(XII)

wherein $R^1$, $R^2$, $R^3$, W, X, Y and Z are as defined in Table I, and each $R^e$ is hydrogen unless indicated otherwise in Table I, or a pharmaceutically-acceptable salt or solvate or stereoisomer thereof.

TABLE I

| Ex. No. | $R^1$ | $R^2$ | $R^3$—O |
|---|---|---|---|
| 1 | —(CH$_2$)$_7$— | isopropyl | (4-methoxypyrid-3-yl)methyl |
| 2 | —(CH$_2$)$_3$—O—(CH$_2$)$_3$— | isopropyl | (4-methoxypyrid-3-yl)methyl |
| 3 | —(CH$_2$)$_4$—O—(CH$_2$)$_2$— | isopropyl | (4-methoxypyrid-3-yl)methyl |
| 4 | —(CH$_2$)$_7$— | ethyl | (2-methoxypyrid-3-yl)methyl |
| 5 | —(CH$_2$)$_7$— | ethyl | (3-methoxypyrid-2-yl)methyl |
| 6 | —(CH$_2$)$_7$— | ethyl | (4-methoxypyrid-3-yl)methyl |
| 7 | —(CH$_2$)$_3$—O—(CH$_2$)$_3$— | ethyl | (4-methoxypyrid-3-yl)methyl |
| 8 | —(CH$_2$)$_8$— | ethyl | (4-methoxypyrid-3-yl)methyl |
| 9 | —(CH$_2$)$_9$— | ethyl | (4-methoxypyrid-3-yl)methyl |
| 10 | —(CH$_2$)$_2$—O—(CH$_2$)$_4$— | ethyl | (4-methoxypyrid-3-yl)methyl |
| 11 | —(CH$_2$)$_2$—O—(CH$_2$)$_5$— | ethyl | (4-methoxypyrid-3-yl)methyl |
| 12 | —(CH$_2$)$_2$—O—(CH$_2$)$_6$— | ethyl | (4-methoxypyrid-3-yl)methyl |
| 13 | —(CH$_2$)$_3$—O—(CH$_2$)$_4$— | ethyl | (4-methoxypyrid-3-yl)methyl |
| 14 | —(CH$_2$)$_3$—O—(CH$_2$)$_5$— | ethyl | (4-methoxypyrid-3-yl)methyl |
| 15 | —(CH$_2$)$_4$—O—(CH$_2$)$_2$— | ethyl | (4-methoxypyrid-3-yl)methyl |
| 16 | —(CH$_2$)$_4$—O—(CH$_2$)$_3$— | ethyl | (4-methoxypyrid-3-yl)methyl |
| 17 | —(CH$_2$)$_4$—O—(CH$_2$)$_4$— | ethyl | (4-methoxypyrid-3-yl)methyl |
| 18 | —(CH$_2$)$_5$—O—(CH$_2$)$_2$— | ethyl | (4-methoxypyrid-3-yl)methyl |
| 19 | —(CH$_2$)$_5$—O—(CH$_2$)$_3$— | ethyl | (4-methoxypyrid-3-yl)methyl |

TABLE I-continued

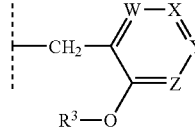

| Ex. No. | R¹ | R² | R³—O |
|---|---|---|---|
| 20 | —(CH$_2$)$_6$—O—(CH$_2$)$_2$— | ethyl | (4-methoxypyrid-3-yl)methyl |
| 21 | —(CH$_2$)$_7$— | n-propyl | (4-methoxypyrid-3-yl)methyl |
| 22 | —(CH$_2$)$_8$— | n-propyl | (4-methoxypyrid-3-yl)methyl |
| 23 | —(CH$_2$)$_9$— | n-propyl | (4-methoxypyrid-3-yl)methyl |
| 24 | —(CH$_2$)$_2$—O—(CH$_2$)$_4$— | n-propyl | (4-methoxypyrid-3-yl)methyl |
| 25 | —(CH$_2$)$_2$—O—(CH$_2$)$_5$— | n-propyl | (4-methoxypyrid-3-yl)methyl |
| 26 | —(CH$_2$)$_2$—O—(CH$_2$)$_6$— | n-propyl | (4-methoxypyrid-3-yl)methyl |
| 27 | —(CH$_2$)$_3$—O—(CH$_2$)$_3$— | n-propyl | (4-methoxypyrid-3-yl)methyl |
| 28 | —(CH$_2$)$_3$—O—(CH$_2$)$_4$— | n-propyl | (4-methoxypyrid-3-yl)methyl |
| 29 | —(CH$_2$)$_3$—O—(CH$_2$)$_5$— | n-propyl | (4-methoxypyrid-3-yl)methyl |
| 30 | —(CH$_2$)$_4$—O—(CH$_2$)$_2$— | n-propyl | (4-methoxypyrid-3-yl)methyl |
| 31 | —(CH$_2$)$_4$—O—(CH$_2$)$_3$— | n-propyl | (4-methoxypyrid-3-yl)methyl |
| 32 | —(CH$_2$)$_4$—O—(CH$_2$)$_4$— | n-propyl | (4-methoxypyrid-3-yl)methyl |
| 33 | —(CH$_2$)$_5$—O—(CH$_2$)$_2$— | n-propyl | (4-methoxypyrid-3-yl)methyl |
| 34 | —(CH$_2$)$_5$—O—(CH$_2$)$_3$— | n-propyl | (4-methoxypyrid-3-yl)methyl |
| 35 | —(CH$_2$)$_6$—O—(CH$_2$)$_2$— | n-propyl | (4-methoxypyrid-3-yl)methyl |
| 36 | —(CH$_2$)$_7$— | isopropyl | (4-n-propoxypyrid-3-yl)methyl |
| 37 | —(CH$_2$)$_7$— | isopropyl | (4-isopropoxypyrid-3-yl)methyl |
| 38 | —(CH$_2$)$_7$— | isopropyl | (4-cyclopropylmethoxypyrid-3-yl)methyl |
| 39 | —(CH$_2$)$_7$— | isopropyl | {4-(2-hydroxyethoxy)pyrid-3-yl}-methyl |
| 40 | —(CH$_2$)$_7$— | isopropyl | (4-isobutoxypyrid-3-yl)methyl |
| 41 | —(CH$_2$)$_7$— | isopropyl | (2,4-dimethoxypyrid-3-yl)methyl |
| 42 | —(CH$_2$)$_7$— | isopropyl | (2-fluoro-4-methoxypyrid-3-yl)-methyl |
| 43 | —(CH$_2$)$_7$— | isopropyl | (2-chloro-4-methoxypyrid-3-yl)-methyl |
| 44 | —(CH$_2$)$_7$— | isopropyl | (2-methyl-4-methoxypyrid-3-yl)-methyl |
| 45 | —(CH$_2$)$_8$— | isopropyl | (4-methoxypyrid-3-yl)methyl |
| 46 | —(CH$_2$)$_9$— | isopropyl | (4-methoxypyrid-3-yl)methyl |
| 47 | —(CH$_2$)$_7$— | isopropyl | (3-methoxypyrid-2-yl)methyl |
| 48 | —(CH$_2$)$_8$— | isopropyl | (3-methoxypyrid-2-yl)methyl |
| 49 | —(CH$_2$)$_9$— | isopropyl | (3-methoxypyrid-2-yl)methyl |
| 50 | —(CH$_2$)$_7$— | isopropyl | (3-methoxypyrid-4-yl)methyl |
| 51 | —(CH$_2$)$_8$— | isopropyl | (3-methoxypyrid-4-yl)methyl |
| 52 | —(CH$_2$)$_9$— | isopropyl | (3-methoxypyrid-4-yl)methyl |
| 53 | —(CH$_2$)$_7$— | isopropyl | (2-methoxypyrid-3-yl)methyl |
| 54 | —(CH$_2$)$_8$— | isopropyl | (2-methoxypyrid-3-yl)methyl |
| 55 | —(CH$_2$)$_9$— | isopropyl | (2-methoxypyrid-3-yl)methyl |
| 56 | —(CH$_2$)$_2$—O—(CH$_2$)$_4$— | isopropyl | (4-methoxypyrid-3-yl)methyl |
| 57 | —(CH$_2$)$_2$—O—(CH$_2$)$_5$— | isopropyl | (4-methoxypyrid-3-yl)methyl |
| 58 | —(CH$_2$)$_2$—O—(CH$_2$)$_6$— | isopropyl | (4-methoxypyrid-3-yl)methyl |
| 59 | —(CH$_2$)$_3$—O—(CH$_2$)$_4$— | isopropyl | (4-methoxypyrid-3-yl)methyl |
| 60 | —(CH$_2$)$_3$—O—(CH$_2$)$_5$— | isopropyl | (4-methoxypyrid-3-yl)methyl |
| 61 | —(CH$_2$)$_4$—O—(CH$_2$)$_3$— | isopropyl | (4-methoxypyrid-3-yl)methyl |
| 62 | —(CH$_2$)$_4$—O—(CH$_2$)$_4$— | isopropyl | (4-methoxypyrid-3-yl)methyl |
| 63 | —(CH$_2$)$_5$—O—(CH$_2$)$_2$— | isopropyl | (4-methoxypyrid-3-yl)methyl |
| 64 | —(CH$_2$)$_5$—O—(CH$_2$)$_3$— | isopropyl | (4-methoxypyrid-3-yl)methyl |
| 65 | —(CH$_2$)$_6$—O—(CH$_2$)$_2$— | isopropyl | (4-methoxypyrid-3-yl)methyl |
| 66 | —(CH$_2$)$_7$— | cyclopropylmethyl | (4-methoxypyrid-3-yl)methyl |
| 67 | —(CH$_2$)$_8$— | cyclopropylmethyl | (4-methoxypyrid-3-yl)methyl |
| 68 | —(CH$_2$)$_9$— | cyclopropylmethyl | (4-methoxypyrid-3-yl)methyl |
| 69 | —(CH$_2$)$_2$—O—(CH$_2$)$_4$— | cyclopropylmethyl | (4-methoxypyrid-3-yl)methyl |
| 70 | —(CH$_2$)$_2$—O—(CH$_2$)$_5$— | cyclopropylmethyl | (4-methoxypyrid-3-yl)methyl |
| 71 | —(CH$_2$)$_2$—O—(CH$_2$)$_6$— | cyclopropylmethyl | (4-methoxypyrid-3-yl)methyl |
| 72 | —(CH$_2$)$_3$—O—(CH$_2$)$_3$— | cyclopropylmethyl | (4-methoxypyrid-3-yl)methyl |
| 73 | —(CH$_2$)$_3$—O—(CH$_2$)$_4$— | cyclopropylmethyl | (4-methoxypyrid-3-yl)methyl |
| 74 | —(CH$_2$)$_3$—O—(CH$_2$)$_5$— | cyclopropylmethyl | (4-methoxypyrid-3-yl)methyl |
| 75 | —(CH$_2$)$_4$—O—(CH$_2$)$_2$— | cyclopropylmethyl | (4-methoxypyrid-3-yl)methyl |
| 76 | —(CH$_2$)$_4$—O—(CH$_2$)$_3$— | cyclopropylmethyl | (4-methoxypyrid-3-yl)methyl |
| 77 | —(CH$_2$)$_4$—O—(CH$_2$)$_4$— | cyclopropylmethyl | (4-methoxypyrid-3-yl)methyl |
| 78 | —(CH$_2$)$_5$—O—(CH$_2$)$_2$— | cyclopropylmethyl | (4-methoxypyrid-3-yl)methyl |
| 79 | —(CH$_2$)$_5$—O—(CH$_2$)$_3$— | cyclopropylmethyl | (4-methoxypyrid-3-yl)methyl |
| 80 | —(CH$_2$)$_6$—O—(CH$_2$)$_2$— | cyclopropylmethyl | (4-methoxypyrid-3-yl)methyl |
| 81 | —(CH$_2$)$_7$— | 2-hydroxyethyl | (4-methoxypyrid-3-yl)methyl |
| 82 | —(CH$_2$)$_8$— | 2-hydroxyethyl | (4-methoxypyrid-3-yl)methyl |
| 83 | —(CH$_2$)$_9$— | 2-hydroxyethyl | (4-methoxypyrid-3-yl)methyl |
| 84 | —(CH$_2$)$_2$—O—(CH$_2$)$_4$— | 2-hydroxyethyl | (4-methoxypyrid-3-yl)methyl |
| 85 | —(CH$_2$)$_2$—O—(CH$_2$)$_5$— | 2-hydroxyethyl | (4-methoxypyrid-3-yl)methyl |
| 86 | —(CH$_2$)$_2$—O—(CH$_2$)$_6$— | 2-hydroxyethyl | (4-methoxypyrid-3-yl)methyl |
| 87 | —(CH$_2$)$_3$—O—(CH$_2$)$_3$— | 2-hydroxyethyl | (4-methoxypyrid-3-yl)methyl |
| 88 | —(CH$_2$)$_3$—O—(CH$_2$)$_4$— | 2-hydroxyethyl | (4-methoxypyrid-3-yl)methyl |
| 89 | —(CH$_2$)$_3$—O—(CH$_2$)$_5$— | 2-hydroxyethyl | (4-methoxypyrid-3-yl)methyl |
| 90 | —(CH$_2$)$_4$—O—(CH$_2$)$_2$— | 2-hydroxyethyl | (4-methoxypyrid-3-yl)methyl |

TABLE I-continued

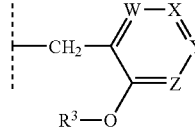

| Ex. No. | R¹ | R² | R³—O |
|---|---|---|---|
| 91 | —(CH₂)₄—O—(CH₂)₃— | 2-hydroxyethyl | (4-methoxypyrid-3-yl)methyl |
| 92 | —(CH₂)₄—O—(CH₂)₄— | 2-hydroxyethyl | (4-methoxypyrid-3-yl)methyl |
| 93 | —(CH₂)₅—O—(CH₂)₂— | 2-hydroxyethyl | (4-methoxypyrid-3-yl)methyl |
| 94 | —(CH₂)₅—O—(CH₂)₃— | 2-hydroxyethyl | (4-methoxypyrid-3-yl)methyl |
| 95 | —(CH₂)₆—O—(CH₂)₂— | 2-hydroxyethyl | (4-methoxypyrid-3-yl)methyl |
| 96 | —(CH₂)₇— | isopropyl | (4-tert-butoxypyrid-3-yl)methyl |
| 97 | —(CH₂)₇— | isopropyl | (4-hydroxypyrid-3-yl)methyl |
| 98 | —(CH₂)₇— | isopropyl | (4-ethoxypyrid-3-yl)methyl |
| 99 | —(CH₂)₇— | isopropyl | (4-trifluoromethoxypyrid-3-yl)-methyl |
| 100 | —(CH₂)₇— | isopropyl | (4-difluoromethoxypyrid-3-yl)-methyl |
| 101 | —(CH₂)₇— | isopropyl | (4-methoxy-2-trifluoro-methoxy-pyrid-3-yl)methyl |
| 102 | —(CH₂)₇— | isopropyl | (2-difluoromethoxy-4-methoxy-pyrid-3-yl)methyl |
| 103 | —(CH₂)₇— | isopropyl | (2-methox-4-trifluoro-methoxy-pyrid-3-yl)methyl |
| 104 | —(CH₂)₇— | isopropyl | (4-difluoromethoxy-2-methoxy-pyrid-3-yl)methyl |
| 105 | —(CH₂)₇— | isopropyl | {2,4-di(trifluoromethoxy)-pyrid-3-yl}methyl |
| 106 | —(CH₂)₇— | isopropyl | {2,4-di(difluoromethoxy)-pyrid-3-yl}methyl |
| 107 | —(CH₂)₇— | isopropyl | (2-ethoxy-4-trifluoro-methoxy-pyrid-3-yl)methyl |
| 108 | —(CH₂)₇— | isopropyl | (2-ethoxy-4-difluoromethoxy-pyrid-3-yl)methyl |
| 109 | —(CH₂)₇— | isopropyl | (2,4-diethoxypyrid-3-yl)methyl |
| 110 | —(CH₂)₇—N(Rᵉ)₂ = —N(H)CH₃ | isopropyl | (4-methoxypyrid-3-yl)methyl |
| 111 | —(CH₂)₇—N(Rᵉ)₂ = —N(CH₃)₂ | isopropyl | (4-methoxypyrid-3-yl)methyl |
| 112 | —(CH₂)₇—N(Rᵉ)₂ = —N(H)Et | isopropyl | (4-methoxypyrid-3-yl)methyl |
| 113 | —(CH₂)₇—N(Rᵉ)₂ = piperidin-1-yl | isopropyl | (4-methoxypyrid-3-yl)methyl |
| 114 | —(CH₂)₇—N(Rᵉ)₂ = morpholin-4-yl | isopropyl | (4-methoxypyrid-3-yl)methyl |
| 115 | —(CH₂)₇— | isopropyl | [4-(2-fluoroethoxy)pyrid-3-yl]-methyl |

[1]In compound 97, the (4-hydroxypyrid-3-yl)methyl group may exist partially or fully as the tautomer, i.e., (pyrid-4-one-3-yl)methyl.

Those of skill in the art will appreciate that the reagents and synthetic conditions described herein can be used to synthesize any of the compounds described in the embodiments, supra.

In the processes of this invention, any suitable reductant may be employed in step (a) and step (c). For example, the reductant used in steps (a) and (c) may be independently chosen from the group consisting of a metal hydride, hydrogen and a noble metal catalyst (i.e., Ni, Pt, Pd, etc.) and an electrochemical anode. Preferably, the reductant used in steps (a) and (c) is independently a metal hydride or hydrogen and a noble metal catalyst, more preferably, a metal hydride. Representative metal hydrides which may be selected independently for use in steps (a) and (c) include, but are not limited to, sodium borohydride, sodium triacetoxyborohydride, sodium cyanoborohydride, borane-pyridine complex, borane-dimethyl sulfide complex, borane-tetrahydrofuran complex, borane-ammonia complex, lithium borohydride, lithium tri-sec-butylborohydride, lithium triethylborohydride, tetrahydro-1-methyl-3,3-diphenyl-1H,3H-pyrrolo-[1,2-c][1,3,2]-oxazaborole, tetramethylammonium triacetoxyborohydride, sodium tris(trifluoroacetoxy)borohydride, sodium dithionite zinc and zinc borohydride. In certain embodiments, the reductant used in steps (a) and (c) is sodium triacetoxyborohydride.

Preferably, step (a) is conducted at a temperature between about −15° C. and about 15° C., more preferably, between about −10° C. and about 10° C. and most preferably, between about −5° C. and about 5° C. Preferably, step (c) is conducted at a temperature between about −15° C. and about 15° C., more preferably, between about −10° C. and about 10° C. and most preferably, between about −5° C. and about 5° C. Suitable diluents for steps (a) and (c) include dichloromethane, acetonitrile and combinations thereof. In some cases, water may also be present in the diluent.

In some embodiments, the acid specified in step (b) is a mineral acid. Examples of mineral acids that may be used in step (b) include, but are not limited to, hydrochloric acid (HCl), sulfuric acid (H₂SO₄), nitric acid (HNO₃), hydrofluoric acid (HF) and phosphoric acid (H₃PO₄). Other suitable mineral acids are known to those of skill in the art. Preferably, the mineral acid used in step (b) is hydrochloric acid.

Preferably, step (b) is conducted at a temperature between about 0° C. and about 30° C., more preferably, between about 5° C. and about 25° C. and most preferably, between about 10° C. and about 20° C.

Preferably, step (b) is conducted at a pH between about 1 and about 4, more preferably, between about 1.5 and about 3.5 and most preferably, between about 2 and about 3.

Compounds of Formula (I) provided by the process described herein are preferably, greater than 95% pure, more preferably, greater than 97% pure, even more preferably, greater than 99% pure and most preferably, greater than 99.5% pure. The purity of the compounds of Formula (I) can be determined using conventional methods, such as HPLC and the like.

In certain embodiments, this invention is directed to a process for preparing a compound of Formula (I) or a salt thereof where each $R^e$ is hydrogen, $R^2$ is isopropyl, $R^3$ is methyl, a is 7, b, c, m, n, q and r are 0, p is 1, W, Y and Z are CH and X is N.

In step (a) of this aspect of the invention, a compound of Formula (VIII):

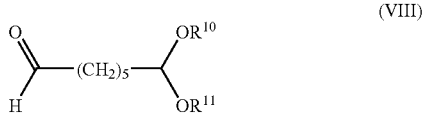

(VIII)

is reacted with a compound of Formula (IX):

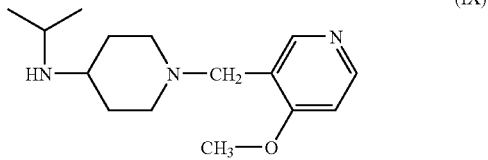

(IX)

and a first reductant to form a compound of Formula (X) or a salt thereof;

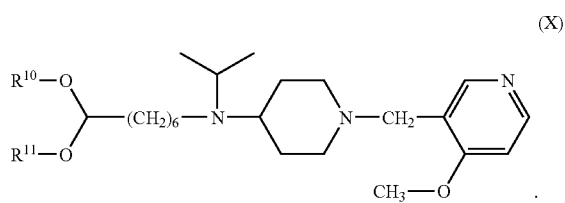

(X)

In step (b), the compound of Formula (X) or a salt thereof is then reacted with acid and water to form a compound of Formula (XI) or a salt thereof:

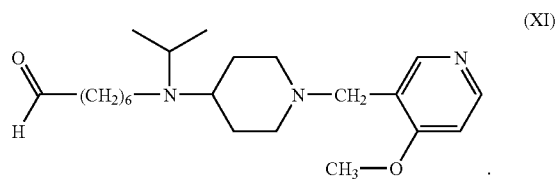

(XI)

In step (c) the compound of Formula (XI) or a salt thereof is reacted with a compound of Formula (XII) or a salt thereof:

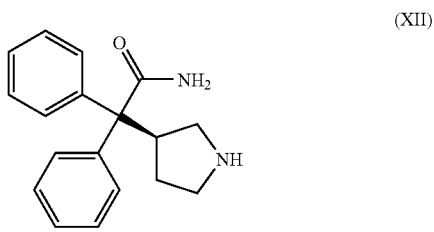

(XII)

and a second reductant to form the compound of Formula (I) or a salt thereof; wherein $R^{10}$ and $R^{11}$ are independently $C_{1-6}$ alkyl; or $R^{10}$ and $R^{11}$ are joined to form $C_{2-6}$ alkylene.

In certain embodiments of this aspect of the invention, the first and second reductant are sodium triacetoxyborohydride. In other embodiments the acid employed in step (b) is hydrochloric acid. In still other embodiments, step (a) is conducted at a temperature in the range from between about −5° C. to about 5° C. In still other embodiments, step (b) is conducted at a temperature in the range from between about 10° C. to about 20° C. In still other embodiments, step (c) is conducted at a temperature in the range from between about −5° C. to about 5° C. In still other embodiments, step (b) is conducted at a pH in the range from between about 2 to about 3.

After formation of the compound of Formula (I), the compound may optionally be purified, either before or after isolation, using one or more extraction procedures. In one such embodiment, an aqueous solution comprising a hydrogen addition salt of the compound of Formula (I) is first prepared. Typically, this solution is prepared by contacting the compound of Formula (I) with water and a sufficient amount of an acid such that the hydrogen additional salt of the compound of Formula (I) is formed. Any suitable acid may be employed including mineral acids, such as hydrochloric acid, sulfuric acid, phosphoric acid and the like. In one embodiment, hydrochloric acid is used in an amount sufficient to prepare an aqueous acidic solution having a pH in the range of about 2 to about 3. In another embodiment, phosphate buffer solution is employed having a pH of about 6.9 to about 7.3, such as about 7.1.

After forming the aqueous solution, the solution is then contacted with a water-immiscible organic diluent. Without wishing to be limited by any theory, it is believed that the water-immiscible organic diluent dissolves any non-basic impurities which have not dissolved in the aqueous solution. Any suitable water-immiscible organic diluent may be employed in this step including, by way of illustration, methyl tert-butyl ether, diethyl ether, ethyl acetate, dichloromethane and the like. Typically, to conduct this step of the process, the water-immiscible organic diluent is contacted with the aqueous solution and the resulting mixture is thoroughly mixed, stirred or agitated for about 0.25 to about 6 hours at a temperature in the range of about 0° C. to about 30° C. The layers are then allowed to separate, typically for at least about 30 minutes, and the water-immiscible organic diluent layer is separated from the aqueous solution layer. If desired, this step of the process may be repeated, typically from 1 to 5, or from 1 to 3 times, or until essentially all of the non-basic impurities are removed.

If desired, the aqueous layer can then be neutralized with a base including, for example, an alkali metal hydroxide such as sodium hydroxide or potassium hydroxide. Typically, this step is conducted by adding a aqueous alkali metal hydroxide solution to the aqueous solution containing the hydrogen addition salt of the compound of Formula (I) until the pH of the resulting solution is about 11 to about 12. Generally, the aqueous alkali metal hydroxide solution is added at such a rate so as to maintain the temperature at less than about 20° C., such as from about 0° C. to about 20° C. During the neutralization procedure, a water-immiscible organic diluent, such as methyl tert-butyl ether, diethyl ether, ethyl acetate, dichloromethane and the like, is typically present in contact with the aqueous acidic solution. As the hydrogen addition salt of the compound of Formula (I) is neutralized, the compound of Formula (I) dissolves in the water-immiscible organic diluent to form a solution comprising the compound of Formula (I) and the water-immiscible organic diluent.

In another embodiment, the compound of Formula (I) may optionally be further purified by contacting a water-immiscible organic diluent solution comprising the compound of Formula (I) and the water-immiscible organic diluent with an aqueous solution comprising an alkali metal carbonate and an alkali metal bisulfite or metabisulfite. While not intending to be limited by any theory, it is believed that the bisulfite or metabisulfite used in this process removes any remaining aldehyde starting material or other aldehyde-containing impurities from the compound of Formula (I). Any suitable alkali metal carbonate and alkali metal bisulfite or metabisulfite may be employed including sodium carbonate, potassium carbonate, sodium bisulfite, sodium metabisulfite, potassium bisulfite, potassium metabisulfite or mixtures of, for example, sodium bisulfite and sodium metabisulfite. Generally, about a 1:1 weight ratio of alkali metal carbonate to alkali metal bisulfite or metabisulfite is employed. When conducting this step, aqueous solution comprising the alkali metal carbonate and the alkali metal bisulfite or metabisulfite is contacted with the water-immiscible organic diluent solution comprising the compound of Formula (I) and the resulting mixture is thoroughly mixed, stirred or agitated for about 0.5 to about 6 hours at a temperature in the range of about 0° C. to about 30° C. The layers are then allowed to separate, typically for at least about 30 minutes, and the water-immiscible organic diluent layer is separated from the aqueous acidic layer. This step of the process may be repeated, typically from 1 to 3 times if desired.

The compounds of Formula (I) may also be converted to napthalene-1,5-disulfonic acid salts. In this embodiment, i.e., in step (j), a compound of Formula (I) is contacted with napthalene-1,5-disulfonic acid or a hydrate thereof to form a napthalene-1,5-disulfonic acid salt of the compound of Formula (I)

The molar ratio of naphthalene-1,5-disulfonic acid to compounds of Formula (I) ranges from about 0.7 to about 1.1; including about 0.8 to about 1.05; and about 0.9 to about 1. Other ranges for the molar ratio include about 0.7 to about 1.05; about 0.7 to about 1; about 0.7 to about 0.95; about 0.8 to about 1.1; about 0.8 to about 1; about 0.8 to about 0.95; about 0.9 to about 1.1; about 0.9 to about 1.05, about 0.9 to about 0.95; about 0.95 to about 1.05; and about 0.95 to about 1.

The molar ratio of naphthalene-1,5-disulfonic acid to compounds of Formula (I) can be readily determined by various methods available to those skilled in the art. For example, such molar ratios can be determined by $^1$H NMR. When using $^1$H NMR, the molar ratio is typically determined by comparing the integration for the naphthalene ring protons of the naphthalene-1,5-disulfonic acid to the integration for the pyridine ring protons in the compound of formula I. Alternatively, elemental analysis and HPLC methods can be used to determine the molar ratio.

Naphthalene-1,5-disulfonic acid (also known as Armstrong's Acid) is commercially available from, for example, Aldrich, Milwaukee, Wis. In one embodiment, the naphthalene-1,5-disulfonic acid employed in this invention is a hydrate, such as the tetrahydrate.

To prepare salts, a compound of Formula (I) is typically contacted with about 0.7 to about 1.1 molar equivalents of naphthalene-1,5-disulfonic acid or a hydrate thereof. Generally, this reaction is conducted in an inert diluent at a temperature ranging from about −20° C. to about 40° C.; including about 0° C. to about 20° C., such as about 2° C. to about 15° C. Suitable inert diluents for this reaction include, but are not limited to, methanol, ethanol, isopropanol, isobutanol, ethyl acetate and the like.

Upon completion of the reaction, the compound of Formula (I) is isolated from the reaction mixture by any conventional means, such as precipitation, concentration, centrifugation and the like.

In certain embodiments, the resulting salts are an amorphous powder. Such amorphous powders are typically prepared by (1) forming a solution of the salt in a first inert diluent in which the salt is readily soluble (i.e., typically having a solubility greater than about 50 mg/mL); and then (2) contacting this solution with a second inert diluent (which can be a combination of inert diluents) in which the salt has lower or no solubility (i.e., typically having a solubility less than about 1 mg/mL), to form a precipitate.

Suitable first inert diluents for forming a solution of the salt include, but are not limited to, methanol, ethanol, isopropanol and the like, or combinations thereof. Generally, the salt is dissolved in the minimum amount of the first inert diluent necessary to form an essentially homogeneous solution.

Suitable second inert diluents for precipitating the salt include, but are not limited to, methy tert-butyl ether, isopropyl acetate and the like, or combinations thereof with isopropanol. In one embodiment, a 2:1 v/v mixture of isopropanol and methyl tert-butyl ether is employed as the second inert diluent.

If desired, the solution of the salt in the first inert diluent can be treated with activated carbon prior to adding the solution to the second inert diluent. Typically, the activated carbon is added to the solution and the resulting mixture is mixed, stirred or agitated for about 0.5 to about 2 hours at a temperature ranging from 0° C. to about 30° C. The mixture is then filtered to remove the activated carbon and any other insoluble materials that may be present.

To form the amorphous powder, a solution of the salt dissolved in the first inert diluent is typically added slowly to the second inert diluent to form a precipitate. This process is typically conducted at a temperature ranging from about 0° C. to about 10° C.; such as about 2° C. to about 8° C. The rate of addition typically ranges from about 50 mL/minute to about 70 mL/minute for a solution containing about 0.20 g/mL to about 0.40 g/mL of the salt to be precipitated.

After formation, the precipitate is isolated using conventional procedures, such as filtration and the like, to provide the amorphous powder. If desired, the precipitate can be washed with an inert diluent, such as methyl tert-butyl ether, and then thoroughly dried.

Further details regarding the specific reaction conditions and other procedures for utilizing the present processes and intermediates are described in the Examples set forth below.

EXAMPLES

The following examples are intended to illustrate various aspects and embodiments of the present and are not to be construed in any way as limiting the scope of the invention unless specifically indicated.

Example A

Synthesis of 4-Isopropylamino-1-(4-methoxypyrid-3-ylmethyl)piperidine Monobenzoic Acid Salt Step A—Preparation of 1-Benzyl-4-isopropylaminopiperidine To a 50 L 3-neck round-bottom reaction flask equipped with a mechanical stirrer, temperature probe, nitrogen inlet and cooling bath was added 4-amino-1-benzylpiperidine (2,000 g, 10.5 mol) and dichloromethane (20 L). Acetone (610.5 g, 10.5 mol) was added and the reaction mixture was stirred at room temperature for 2.5 hours. The reaction mixture was then cooled to 0° C. to 5° C. with an ice/methanol bath and sodium triacetoxyborohydride (2,673 g, 12.6 mol) was added while maintaining the temperature of the reaction mixture below 25° C. The cooling bath was then removed and the reaction mixture was stirred until less than 1% starting material was present by gas chromatograhy (GC) analysis (about 3 hours). Concentrated hydrochloric acid was added until the pH of the reaction mixture was 7 (about 500 mL). The resulting slurry was filtered through a polypropylene filter pad and the solids were washed with dichloromethane (2×2 L). The solids were saved for use after concentration of the filtrate. The filtrate was concentrated at 40° C. until no condensate remained. In a 40 L separatory funnel, the solids and distillation residue were dissolved in water (15 L) and concentrated hydrochloric acid was added until the pH of the solution was 3 (about 2.5 L). The aqueous layer was then washed with dichloromethane (2×2 L). The pH of the aqueous layer was adjusted to 11 to 12 with 50% aqueous sodium hydroxide solution (about 4.5 L) and this mixture was extracted with dichloromethane (5×3 L). The organic layers were combined, decolorized with charcoal (50 g) and dried over anhydrous magnesium sulfate (200 g). The solids were filtered off using a glass fiber filter pad and the filtrate was concentrated until no condensate remained to afford the title compound (2,336 g, 96% yield).

Step B—Preparation of 4-Isopropylaminopiperidine

The product from Step A (18 g, 77 mmol) and methanol (200 mL) were added to a 500 mL round-bottom flask and the resulting mixture was stirred until a clear solution was obtained. Palladium on carbon (400 mg, 10%) in methanol (2 mL) was then added and the reaction mixture was placed under a hydrogen-filled balloon and stirred at ambient temperature for 18 hours. The reaction mixture was then filtered through a Celite pad to remove the catalyst and the filtrate was concentrated on a rotary evaporator to afford the title compound as a yellow-colored oil (11 g, quantitative yield).

Step C—Preparation of 4-Isopropylamino-1-(4-methoxyperid-3-ylmethyl)piperidine

4-Isopropylaminopiperidine (1.32 g, 9.3 mmol) and dichloromethane (40 mL) were added to a 100 mL round-bottom flask equipped with a cooling bath. 4-Methoxypyridine-3-carboxaldehyde (1.44 g, 10.5 mmol) (prepared, for example, as described in U.S. patent application No. 2004/0122014 A1) was added and the reaction mixture was stirred at room temperature for 1 hour. The reaction mixture was then cooled to 0° C. to 5° C. using a methanol/ice bath and sodium triacetoxyboerohydride (2.54 g, 12 mmol) was added at such a rate so as to maintain the temperature of the reaction mixture less than 10° C. When the addition was complete, the reaction mixture was stirred at ambient temperature until less than 1% starting material was present by GC analysis (about 3 hours). Aqueous 1N hydrochloric acid (20 mL) was then added and the layers were separated. The pH of aqueous layer was adjusted to 12 with aqueous 50% sodium hydroxide solution and the resulting mixture was stirred for 1 hour. The aqueous layer was then extracted with ethyl acetate (2×20 L) and the combined organic layers were decolorized with charcoal (1 g) and dried over anhydrous magnesium sulfate (5 g). The solids were removed by filtration through a glass fiber filter pad and the filtrate was concentrated under vacuum. The residue was further dried under high vacuum for 1 hour to give the title compound (2.1 g, 80% yield).

Step D—Preparation of 4-Isopropylamino-1-(4-methoxypyrid-3-ylmethyl)piperidine Monobenzoic Acid Salt Benzoic acid (1451 g, 11.9 mol) and MTBE (5.8 L) were added to a 50 L 3-necked round-bottom flask equipped with a mechanical stirrer, thermometer, nitrogen inlet and heating mantle. The resulting slurry was heated at 45° C. to 50° C. to dissolve the benzoic acid. A solution of 4-isopropylamino-1-(4-methoxypyrid-3-ylmethyl)piperidine (3130 g, 11.9 mol) in methy tert-butyl ether (MTBE) (13.7 L) was added at 45° C. to 50° C. and the resulting mixture was stirred at reflux (50° C. to 55° C.) for 30 minutes and then at ambient temperature for 16 hours. The reaction mixture was then cooled to 0° C. to 5° C. with an ice/methanol bath and stirred for 30 minutes at which time a solid had formed. The solid was filtered through a polypropylene filter pad and washed with MTBE (3×2 L) and ethyl ether (3×2 L). The solid was then tray dried in a vacuum oven at room temperature until a constant weight was obtained to provide the title compound (3805 g, 82% yield).

Example 1

Synthesis of 4-{N-[7-(3-(S)-1-Carbamoyl-1,1-diphenylmethyl)-pyrrolidin-1-yl)hept-1-yl]-N-(isopropyl)amino}-1-(4-methoxypyrid-3-ylmethyl)piperidine Naphthalene-1,5-disulfonic Acid Salt Step A—Preparation of (7,7-Dimethoxyheptyl)isopropyl-[1-(4-methoxypyridin-3-ylmethyl)piperidin-4-yl]amine To a reactor containing dichloromethane (4 L) was added 4-isopropylamino-1-(4-methoxypyrid-3-ylmethyl)piperidine monobenzoic acid salt (1.5 kg, 3.89 mol) while maintaining the temperature of the mixture at –5° C. to 5° C. The container used to add the salt was rinsed with dichloromethane (1.5 L) and the rinse was added to the reaction mixture. The temperature of the reaction mixture was then adjusted to 0° C. to 5° C. and 7,7-dimethoxyheptanal (790 g, 4.25 mol, 93.8% purity by GC) was added while maintaining the temperature of the reaction mixture between 0° C. to 5° C. The container used to add the 7,7-dimethoxyheptanal was rinsed with dichloromethane (0.8 L) and the rinse was added to the reactor. The resulting reaction mixture was then stirred at 0° C. to 5° C. for 1 hour. Sodium triacetoxyborohydride (1.07 kg, 5.05 mol) was then added in 7 equal portions over a period of 1 hour while maintaining the temperature of the reaction mixture between –5° C. to 5° C. The container used to add the sodium triacetoxyborohydride was rinsed with dichloromethane (0.8 L) and the rinse was added to the reaction mixture. The reaction mixture was then stirred at 0° C. to 5° C. for 21 hours. An aqueous solution of potassium carbonate (500 g) in deionized water (8.6 L) was then added to the reaction mixture while maintaining the temperature of the mixture between to 0° C. to 25° C. The resulting mixture was stirred for 2 hours at a temperature between 15° C. to 25° C. The layers were then allowed to separate over a period of 30 minutes and the organic layer was collected. The washing procedure with aqueous potassium carbonate solution was repeated 2 times. To the organic layer was then added an aqueous solution of sodium chloride (5.7 kg) in deionized water (15 L) while maintaining the temperature between to 15° C. to 25° C. The resulting mixture was stirred for 30 minutes at a temperature between 15° C. to 25° C. and then the layers were allowed to separate over a period of 30 minutes. The organic layer was collected and to this layer was added dichloromethane (1.5 L). The resulting solution containing the title compound was stored under a nitrogen atmosphere, protected from light, at 0° C. to 5° C. until used in the subsequent reaction.

Step B—Preparation of 7-{Isopropyl-[1-(4-methoxypyridin-3-ylmethyl)-piperidin-4-yl]amino}heptanal The temperature of the solution from Step A was adjusted to 5° C. to 15° C. and an aqueous hydrochloric acid solution (prepared by adding 1.4 L of concentrated hydrochloric acid to 14.2 L of deionized water) was added while maintaining the temperature of the reaction mixture below 20° C. The resulting two-phase mixture was stirred at 15° C. to 25° C. for 11 hours. The mixture was allowed to stand without stirring for a period of 30 minutes and the organic layer was removed. To the aqueous layer was added dichloromethane (6 L) and this mixture was stirred for 30 minutes. The layers were then allowed to separate over a period of 30 minutes and the organic layer was removed. This washing procedure of the aqueous layer with dichloromethane was repeated 2 additional times. The resulting aqueous solution containing the title compound was stored under a nitrogen atmosphere, protected from light, at 0° C. to 5° C. until used in the subsequent reaction.

Step C—Preparation of 4-{N-[7-(3-(S)-1-Carbamoyl-1,1-diphenylmethyl)-pyrrolidin-1-yl]hept-1-yl]-N-(isopropyl)amino}-1-(4-methoxypyrid-3-ylmethyl)-piperidine The temperature of the solution from Step B was adjusted to –5° C. to 5° C. and an aqueous sodium hydroxide solution (prepared by dissolving 230 g of sodium hydroxide in 2.9 L of deionized water) was added while maintaining the temperature of the reaction mixture in the range of –5° C. to 5° C. Acetonitrile (9.3 L) was then added while maintaining the temperature of the reaction mixture in the range of –5° C. to 5° C. (S)-3-(1-Carbamoyl-1,1-diphenylmethyl)pyrrolidine (988 g, 3.52 mol) (prepared, for example, as described in U.S. patent application No. 2004/0122014 A1) was then added and the resulting mixture was stirred at –5° C. to 5° C. for 1 hour. Sodium triacetoxyborohydride (853 g, 4.02 mol) was then added in 7 equal portions over a period of 1 hour while maintaining the temperature of the reaction mixture between –5° C. to 5° C. The reaction mixture was then stirred at 0° C. to 5° C. for 4.25 hours. Concentrated hydrochloric acid (8.2 L) was then added to the reaction mixture until the pH was in the range of from 2 to 3 while maintaining the temperature below 20° C. MTBE (9.8 L) was then added and the resulting mixture was stirred for 45 minutes at 15° C. to 25° C. The mixture was allowed to stand without stirring for a period of 30 minutes and the aqueous layer was separated. This washing procedure of the aqueous layer with MTBE was repeated and then MTBE (19.4 L) was added to the aqueous layer. An aqueous sodium hydroxide solution (prepared by dissolving 910 g of sodium hydroxide in 5.7 L of deionized water) was added until the pH of the aqueous layer was 11 to 12 while maintaining the temperature below 20° C. This mixture was stirred for 30 minutes at 15° C. to 25° C. The layers were then allowed to separate over a period of 30 minutes and the layers were separated. To the organic layer was added an aqueous solution of potassium carbonate and sodium metabisulfite (prepared by dissolving 970 g of potassium carbonate and 970 g of sodium metabisulfite in 19.4 L of deionized water) and the resulting mixture was stirred for 3 hours at 15° C. to 25° C. The mixture was allowed to stand without stirring for a period of 30 minutes and the layers were separated. To the organic layer was added an aqueous solution of sodium bicarbonate (prepared by dissolving 1.4 kg of sodium bicarbonate in 15 L of deionized water) and the resulting mixture was stirred for 30 minutes at 15° C. to 25° C. The mixture was allowed to stand without stirring for a period of 30 minutes and then the layers were separated. To the organic layer was added deionized water (15 L) and the resulting mixture was stirred for 30 minutes at 15° C. to 25° C. The mixture was allowed to stand without stirring for a period of 30 minutes and then the layers were separated. To the organic layer was added an aqueous phosphate buffer solution (7.5 L) (prepared by mixing a solution of 2.396 kg of sodium hydrogen phosphate dissolved in 67.5 L of deionized water with a solution of 675 g of sodium dihydrogen phosphate dissolved in 22.5 L of deionized water) and the resulting mixture was stirred for 30 minutes at 15° C. to 25° C. The mixture was allowed to stand for 10 minutes and then the layers were separated. This procedure was repeated 11 times and then the aqueous layers of appropriate purity were combined. To the combined aqueous layers was added MTBE (19.4 L) and then an aqueous sodium hydroxide solution (prepared by dissolving 290 g of sodium hydroxide in 1.8 L of deionized water) was added while maintaining the temperature below 20° C. until the pH of the aqueous layer was 11 to 12. This mixture was stirred for 30 minutes at 15° C. to 25° C. The mixture was allowed to stand without stirring for a period of 30 minutes and the layers were separated. To the organic layer was added deionized water (15 L) and the resulting mixture was stirred for 1.5 hours at 15° C. to 25° C. The mixture was allowed to stand without stirring for a period of 1 hour and then the layers were separated. To the organic layer was added anhydrous magnesium sulfate (3 kg) and the resulting mixture was stirred for 2.25 hours at 15° C. to 30° C. The mixture was then filtered and the filter cake was washed with MTBE (4.5 L). The resulting solution containing the title compound was stored under a nitrogen atmosphere, protected from light, at 0° C. to 5° C. until being used in the subsequent reaction.

Step D—Preparation of 4-{N-[7-(3-(S)-1-Carbamoyl-1,1-diphenylmethyl)-pyrrolidin-1-yl]hept-1-yl]-N-(isopropyl)amino}-1-(4-methoxypyrid-3-ylmethyl)-piperidine Naphthalene-1,5-disulfonic Acid Salt To methanol (6 L) was added naphthalene-1,5-disulfonic acid (641.33 g, 2.22 mol) and the resulting mixture was stirred until the naphthalene-1,5-disulfonic acid completely dissolved. To this solution was added isopropanol (6 L) and the temperature of the resulting mixture was adjusted to 15° C. to 25° C. MTBE (11 L) and isopropanol (57 L) were added to the solution from Step C and then the solution of naphthalene-1,5-disulfonic acid was added over a period of 2 hours while maintaining the temperature of the reaction mixture at 15° C. to 25° C. Isopropanol (6 L) was then added while maintaining the temperature of the reaction mixture at 15° C. to 25° C. and the resulting mixture was stirred for 12 hours at a temperature in the range of 15° C. to 25° C. The mixture was then cooled to a temperature of 0° C. to 5° C. and stirred for 2 hours. The precipitate which formed was then collected by filtration under nitrogen and the filter cake was washed three times with MTBE (6 L) cooled to 0° C. to 5° C. The precipitate was then dried under vacuum at ambient temperature to provide the title compound (1,452.6 g, 40% overall yield, 99.6% purity by HPLC).

Example 1 demonstrates that the present process provides a compound of Formula (I) (i.e., 4-{N-[7-(3-(S)-1-carbamoyl-1,1-diphenylmethyl)-pyrrolidin-1-yl)-hept-1-yl]-N-(isopropyl)amino}-1-(4-methoxypyrid-3-ylmethyl)-piperidine as its naphthalene-1,5-disulfonic acid salt) from a compound of Formula (III) (i.e., 4-isopropylamino-1-(4-methoxypyrid-3-ylmethyl)piperidine monobenzoic acid salt) in high yield (i.e., 40% overall) and with high purity (i.e., 99.6%) without the need for isolation of intermediates or chromatographic purification.

Finally, those skilled in the art will appreciate that there are alternative ways of implementing the present invention.

Accordingly, the present embodiments are to be considered as illustrative and not restrictive, and the invention is not to be limited to the details given herein, but may be modified within the scope and equivalents of any claim(s) issuing herefrom. All publications and patents cited herein are incorporated by reference in their entirety to the extent permitted by applicable patent statutes and regulations.

What is claimed is:

1. A process for preparing a compound of Formula (I):

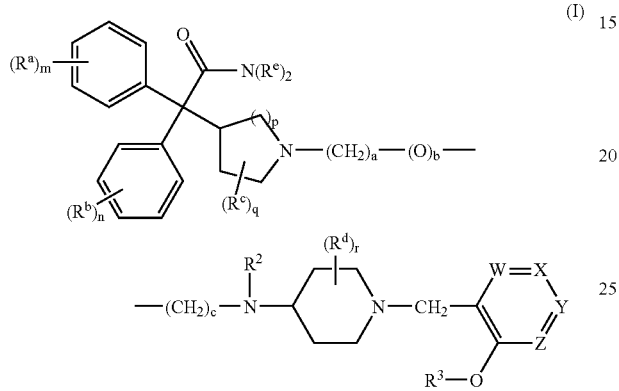

the process comprising:
(a) reacting a compound of Formula (II);

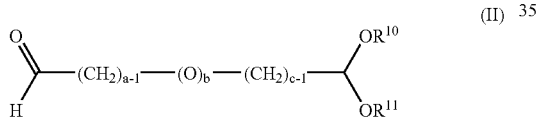

with a compound of Formula (III) or a salt thereof;

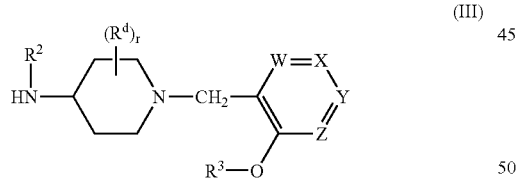

and a first reductant to form a compound of Formula (IV) or a salt thereof;

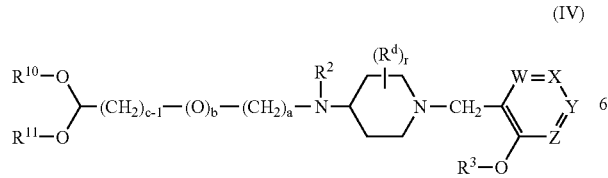

(b) reacting the compound of Formula (IV) or a salt thereof with an acid and water to form a compound of Formula (V) or a salt thereof;

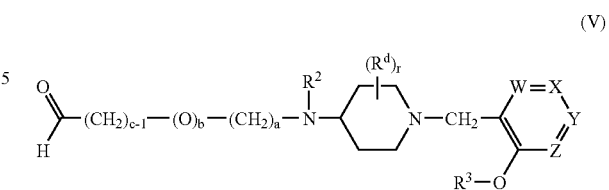

(c) reacting the compound of Formula (V) or a salt thereof with a compound of Formula (VI) or a salt or stereoisomer thereof;

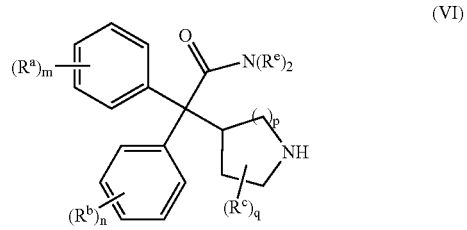

and a second reductant to form the compound of Formula (I) or a salt or stereoisomer thereof;

wherein

W, X, Y and Z are independently selected from the group consisting of CH, $CR^4$, N and N→O; provided that at least one and no more than two of W, X, Y and Z are N or N→O;

$R^2$ is selected from the group consisting of hydrogen, $C_{1-6}$ alkyl, $C_{2-6}$ alkenyl, $C_{2-6}$ alkynyl, $C_{3-6}$ cycloalkyl, —$CH_2$—$R^5$ and —$(CH_2)_x$—$R^6$; wherein each alkyl, alkenyl, alkynyl and cycloalkyl group is optionally substituted with 1 to 5 fluoro substituents;

each $R^3$ is independently selected from the group consisting of hydrogen, $C_{1-6}$ alkyl, $C_{2-6}$ alkenyl, $C_{2-6}$ alkynyl, $C_{3-6}$ cycloalkyl, —$CH_2R^7$ and —$(CH_2)_y$—$R^8$ wherein each alkyl, alkenyl, alkynyl and cycloalkyl group is optionally substituted with 1 to 5 fluoro substituents;

each $R^4$ is independently selected from the group consisting of $C_{1-6}$ alkyl, $C_{2-6}$ alkenyl, $C_{2-6}$ alkynyl, $C_{3-6}$ cycloalkyl, —$OR^3$ and halo or two adjacent $R^4$ groups are joined to form $C_{3-6}$ alkylene, —O—($C_{2-4}$ alkylene)-, —O—($C_{1-4}$ alkylene)-O—, —(O)C—CH=CH— or —CH=CH—C(O)— or when Z is $CR^4$, —$OR^3$ and $R^4$ are joined to form —O—($C_{2-5}$ alkylene)- or —O—($C_{1-5}$ alkylene)-O— wherein each alkyl, alkylene, alkenyl, alkynyl and cycloalkyl group is optionally substituted with 1 to 5 fluoro substituents;

each $R^5$ and $R^7$ is independently selected from the group consisting of $C_{3-5}$ cycloalkyl, $C_{6-10}$ aryl, —C(O)($C_{6-10}$ aryl), $C_{2-9}$ heteroaryl, —C(O)($C_{2-9}$ heteroaryl) and $C_{3-6}$ heterocyclic wherein the cycloalkyl group is optionally substituted with 1 to 5 fluoro substituents and the aryl, heteroaryl and heterocyclic groups are optionally substituted with 1 to 3 substituents independently selected from $R^k$ and the aryl and heteroaryl groups are optionally further substituted with a phenyl group, where the phenyl group is optionally substituted with 1 to 3 substituents independently selected from $R^k$;

each $R^6$ and $R^8$ is independently selected from the group consisting of —OH, —$OR^9$, —$SR^9$, —$S(O)R^9$, —$S(O)_2R^9$, —$C(O)R^9$, $C_{3-5}$ cycloalkyl, $C_{6-10}$ aryl, $C_{2-9}$ heteroaryl and $C_{3-6}$ heterocyclic wherein the cycloalkyl group is optionally substituted with 1 to 5 fluoro substituents; and the aryl, heteroaryl and heterocyclic groups are optionally substituted with 1 to 3 substituents independently selected from $R^k$;

each $R^g$ is independently selected from the group consisting of $C_{1-4}$ alkyl, $C_{3-5}$ cycloalkyl, $C_{6-10}$ aryl and $C_{2-9}$ heteroaryl wherein the alkyl and cycloalkyl groups are optionally substituted with 1 to 5 fluoro substituents; and the aryl and heteroaryl groups are optionally substituted with 1 to 3 substituents independently selected from $R^k$;

$R^{10}$ and $R^{11}$ are independently $C_{1-6}$ alkyl or $R^{10}$ and $R^{11}$ are joined to form $C_{2-6}$ alkylene;

each $R^a$ and $R^b$ is independently selected from the group consisting of $C_{1-4}$ alkyl, $C_{2-4}$ alkenyl, $C_{2-4}$ alkynyl, $C_{3-6}$ cycloalkyl, cyano, halo, —$OR^f$, —$SR^f$, —$S(O)R^f$, —$S(O)_2R^f$ and —$NR^gR^h$; or two adjacent $R^a$ groups or two adjacent $R^b$ groups are joined to form $C_{3-6}$ alkylene, ($C_{2-4}$ alkylene)-O— or —O—($C_{1-4}$ alkylene)-O— wherein each alkyl, alkylene, alkenyl, alkynyl and cycloalkyl group is optionally substituted with 1 to 5 fluoro substituents;

each $R^c$ and $R^d$ is independently selected from the group consisting of $C_{1-4}$ alkyl and fluoro wherein each alkyl group is optionally substituted with 1 to 5 fluoro substituents;

each $R^e$ is independently selected from the group consisting of hydrogen, $C_{1-6}$ alkyl, $C_{2-6}$ alkenyl, $C_{2-6}$ alkynyl, $C_{3-6}$ cycloalkyl, $C_{6-10}$ aryl, $C_{2-9}$ heteroaryl, $C_{3-6}$ heterocyclic, —$CH_2$—$R^i$ and —$CH_2CH_2$—$R^j$ or both $R^e$ groups are joined together with the nitrogen atom to which they are attached to form $C_{3-6}$ heterocyclic; wherein each alkyl, alkenyl, alkynyl and cycloalkyl group is optionally substituted with 1 to 5 fluoro substituents; and each aryl, heteroaryl and heterocyclic group is optionally substituted with 1 to 3 substituents independently selected from $R^k$;

each $R^f$ is independently selected from the group consisting of hydrogen, $C_{1-4}$ alkyl, $C_{2-4}$ alkenyl, $C_{2-4}$ alkynyl and $C_{3-6}$ cycloalkyl wherein each alkyl, alkenyl, alkynyl and cycloalkyl group is optionally substituted with 1 to 5 fluoro substituents;

each $R^g$ and $R^h$ is independently selected from the group consisting of hydrogen, $C_{1-4}$ alkyl, $C_{2-4}$ alkenyl, $C_{2-4}$ alkynyl and $C_{3-6}$ cycloalkyl or $R^g$ and $R^h$ are joined together with the nitrogen atom to which they are attached to form $C_{3-6}$ heterocyclic; wherein each alkyl, alkenyl, alkynyl and cycloalkyl group is optionally substituted with 1 to 5 fluoro substituents, and the heterocyclic group is optionally substituted with 1 to 3 substituents independently selected from $C_{1-4}$ alkyl and fluoro;

each $R^i$ is independently selected from the group consisting of $C_{3-6}$ cycloalkyl, $C_{6-10}$ aryl, $C_{2-9}$ heteroaryl and $C_{3-6}$ heterocyclic; wherein aryl, cycloalkyl, heteroaryl and heterocyclic group is optionally substituted with 1 to 3 substituents independently selected from $R^k$;

each $R^j$ is independently selected from the group consisting of $C_{3-6}$ cycloalkyl, $C_{6-10}$ aryl, $C_{2-9}$ heteroaryl, $C_{3-6}$ heterocyclic, —OH, —O($C_{1-6}$ alkyl), —O($C_{3-6}$ cycloalkyl), —O($C_{6-10}$ aryl), —O($C_{2-9}$ heteroaryl), —S($C_{1-6}$ alkyl), —S(O)($C_{1-6}$ alkyl), —S(O)$_2$($C_{1-6}$ alkyl), —S($C_{3-6}$ cycloalkyl), —S(O)($C_{3-6}$ cycloalkyl), —S(O)$_2$($C_{3-6}$ cycloalkyl), —S($C_{6-10}$ aryl), —S(O)($C_{6-10}$ aryl), —S(O)$_2$($C_{6-10}$ aryl), —S($C_{2-9}$ heteroaryl), —S(O)($C_{2-9}$ heteroaryl) and —S(O)$_2$($C_{2-9}$ heteroaryl) wherein each alkyl group is optionally substituted with 1 to 5 fluoro substituents and each aryl, cycloalkyl, heteroaryl and heterocyclic group is optionally substituted with 1 to 3 substituents independently selected from $R^k$;

each $R^k$ is independently selected from the group consisting of $C_{1-4}$ alkyl, $C_{2-4}$ alkenyl, $C_{2-4}$ alkynyl, cyano, halo, —$OR^f$, —$SR^f$, —$S(O)R^f$, —$S(O)_2R^f$ and —$NR^gR^h$ or two adjacent $R^k$ groups are joined to form $C_{3-6}$ alkylene, —($C_{2-4}$ alkylene)-O— or —O—($C_{1-4}$ alkylene)-O— wherein each alkyl, alkylene, alkenyl and alkynyl group is optionally substituted with 1 to 5 fluoro substituents;

each —$CH_2$— group in a compound of Formula (I) is optionally substituted with one or two substituents independently selected from the group consisting of $C_{1-2}$ alkyl, and fluoro where each alkyl group is optionally substituted with 1 to 3 fluoro groups;

a is an integer from 2 to 7;

b is 0 or 1;

c is an integer from 2 to 7; provided that a+b+c equals 7, 8 or 9;

m is an integer from 0 to 3;

n is an integer from 0 to 3;

p is 1 or 2;

q is an integer from 0 to 4;

r is an integer from 0 to 4;

x is an integer from 2 to 4; and y is an integer from 2 to 4;

wherein each heterocyclic group is independently selected from a pyrrolidine, imidazolidine, pyrazolidine, piperidine, 1,4-dioxane, morpholine, thiomorpholine, piperazine, and 3-pyrroline group; and wherein each heteroaryl group is independently selected from a pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, and quinoxaline group.

2. The process of claim 1, wherein the process further comprises:
(d) forming an aqueous solution comprising a hydrogen addition salt of the compound of Formula (I);
(e) contacting the aqueous solution from step (d) with a water-immiscible organic diluent; and then
(f) separating the water-immiscible organic diluent from the aqueous solution.

3. The process of claim 1, wherein the process further comprises:
(g) forming a water-immiscible organic diluent solution comprising the compound of Formula (I) and a water-immiscible organic diluent;
(h) contacting the water-immiscible organic diluent solution from step (g) with an aqueous solution comprising an alkali metal carbonate and an alkali metal bisulfite or metabisulfite; and then
(i) separating the water-immiscible organic diluent solution from the aqueous solution.

4. The process of claim 2 or 3, wherein the water-immiscible organic diluent is methyl tert-butyl ether.

5. The process of claim 1, wherein the process further comprises:
(j) contacting the compound of Formula (I) with napthalene-1,5-disulfonic acid to form a napthalene-1,5-disulfonic acid salt of the compound of Formula (I).

6. The process of claim 1, wherein b is 0.

7. The process of claim 1, wherein m and n are 0.

8. The process of claim 1, wherein q and r are 0.

9. The process of claim 1, wherein b, m, n, q and r are 0; and p is 1.

10. The process of claim 1, wherein each $R^e$ is hydrogen.

11. The process of claim 1, wherein $R^2$ is $C_{1-4}$ alkyl.

12. The process of claim 1, wherein $R^3$ is $C_{1-4}$ alkyl.

13. The process of claim 1, wherein W, Y and Z are CH and X is N.

14. The process of claim 1, wherein each $R^e$ is hydrogen, $R^2$ is $C_{1-4}$ alkyl, $R^3$ is $C_{1-4}$ alkyl, b, m, n, q and r are 0, p is 1, W, Y and Z are CH and X is N.

15. The process of claim 1, wherein $R^{10}$ and $R^{11}$ are selected independently from $C_{1-3}$ alkyl; or joined together to form $C_{2-4}$ alkylene.

16. The process of claim 1, wherein the first and second reductant are independently a metal hydride reductant or hydrogen and a noble metal catalyst.

17. The process of claim 1, wherein the first and second reductant are independently selected from sodium borohydride, sodium triacetoxyborohydride, sodium cyanoborohydride, borane-pyridine complex, borane-dimethyl sulfide complex, borane-tetrahydrofuran complex, borane-ammonia complex, lithium borohydride, lithium tri-sec-butylborohydride, lithium triethylborohydride, tetrahydro-1-methyl-3,3-diphenyl-1H,3H-pyrrolo[1,2-c][1,3,2]oxazaborole, tetramethylammonium triacetoxyborohydride, sodium tris(trifluoroacetoxy)borohydride, sodium dithionite zinc and zinc borohydride.

18. The process of claim 1, wherein the acid employed in step (b) is a mineral acid.

19. The process of claim 1, wherein step (a) is conducted at a temperature in the range from between about −5° C. to about 5° C.

20. The process of claim 1, wherein step (b) is conducted at a temperature in the range from between about 10° C. to about 20° C.

21. The process of claim 1, wherein step (c) is conducted at a temperature in the range from between about −5° C. to about 5° C.

22. The process of claim 1, wherein step (b) is conducted at a pH in the range from between about 2 to about 3.

23. A process for preparing a compound of Formula (VII):

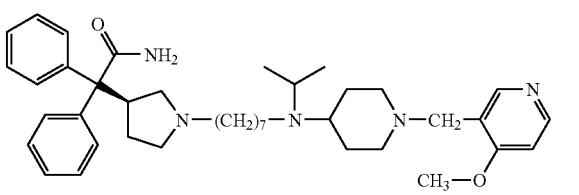

(VII)

or a salt thereof the process comprising:
(a) reacting a compound of Formula (VIII)

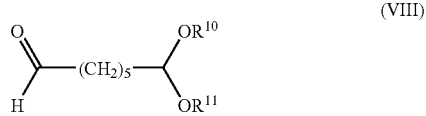

(VIII)

with a compound of Formula (IX) or a salt thereof

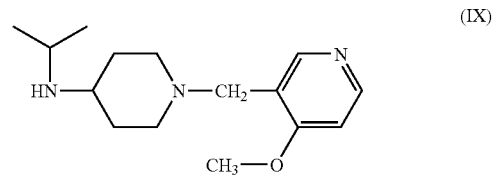

(IX)

and a first reductant to form a compound of Formula (X) or a salt thereof;

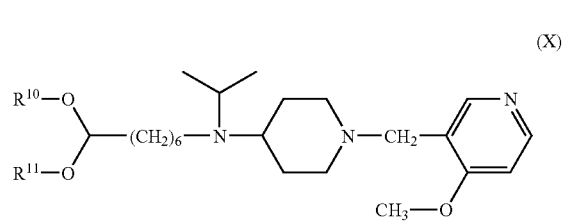

(X)

(b) reacting the compound of Formula (X) or a salt thereof with acid and water to form a compound of Formula (XI) or a salt thereof:

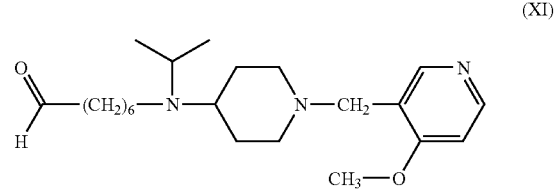

(XI)

(c) reacting the compound of Formula (XI) or a salt thereof with a compound of Formula (XII) or a salt thereof;

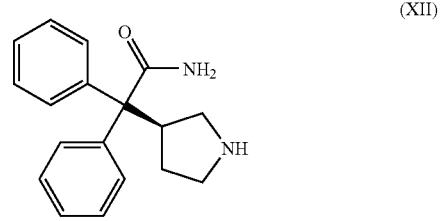

(XII)

and a second reductant to form the compound of Formula (I) or a salt thereof;
wherein $R^{10}$ and $R^{11}$ are independently $C_{1-6}$ alkyl or $R^{10}$ and $R^{11}$ are joined to form $C_{2-6}$ alkylene.

24. The process of claim 23, wherein the process further comprises:
(d) forming an aqueous solution comprising a hydrogen addition salt of the compound of Formula (VII);
(e) contacting the aqueous solution from step (d) with a water-immiscible organic diluent; and then
(f) separating the water-immiscible organic diluent from the aqueous solution.

25. The process of claim 23, wherein the process further comprises:
(g) forming a water-immiscible organic diluent solution comprising the compound of Formula (VII) and a water-immiscible organic diluent;
(h) contacting the water-immiscible organic diluent solution from step (g) with an aqueous solution comprising an alkali metal carbonate and an alkali metal bisulfite or metabisulfite; and then
(i) separating the water-immiscible organic diluent solution from the aqueous solution.

26. The process of claim 23, wherein the process further comprises:
(j) contacting the compound of Formula (VII) with napthalene-1,5-disulfonic acid to form a napthalene-1,5-disulfonic acid salt of the compound of Formula (VII).

27. The process of claims 23, wherein $R^{10}$ and $R^{11}$ are both methyl.

28. The process of claim 23, wherein the first and second reductant are sodium triacetoxyborohydride.

29. The process of claim 23, wherein the acid employed in step (b) is hydrochloric acid.

30. The process of claim 23, wherein step (a) is conducted at a temperature in the range from between about −5° C. to about 5° C.

31. The process of claim 23, wherein step (b) is conducted at a temperature in the range from between about 10° C. to about 20° C.

32. The process of claim 23, wherein step (c) is conducted at a temperature in the range from between about −5° C. to about 5° C.

33. The process of claim 23, wherein step (b) is conducted at a pH in the range from between about 2 to about 3.

34. The process of claim 24 or 25, wherein the water-immiscible organic diluent is methyl tert-butyl ether.

35. A compound of Formula (IV):

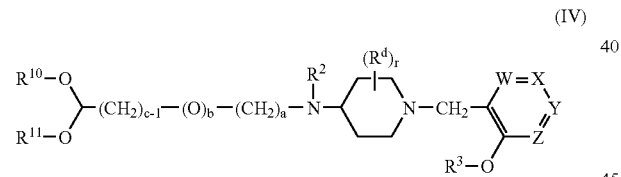

(IV)

or a salt or stereoisomer thereof,
wherein
W, X, Y and Z are independently selected from the group consisting of CH, $CR^4$, N and N→O; provided that at least one and no more than two of W, X, Y and Z are N or N→O;
$R^2$ is selected from the group consisting of hydrogen, $C_{1-6}$ alkyl, $C_{2-6}$ alkenyl, $C_{2-6}$ alkynyl, $C_{3-6}$ cycloalkyl, —$CH_2$—$R^5$ and —$(CH_2)_x$—$R^6$; wherein each alkyl, alkenyl, alkynyl and cycloalkyl group is optionally substituted with 1 to 5 fluoro substituents;
each $R^3$ is independently selected from the group consisting of hydrogen, $C_{1-6}$ alkyl, $C_{2-6}$ alkenyl, $C_{2-6}$ alkynyl, $C_{3-6}$ cycloalkyl, —$CH_2$—$R^7$ and —$(CH_2)_y$—$R^8$ wherein each alkyl, alkenyl, alkynyl and cycloalkyl group is optionally substituted with 1 to 5 fluoro substituents;
each $R^4$ is independently selected from the group consisting of $C_{1-6}$ alkyl, $C_{2-6}$ alkenyl, $C_{2-6}$ alkynyl, $C_{3-6}$ cycloalkyl, —$OR^3$ and halo or two adjacent $R^4$ groups are joined to form $C_{3-6}$ alkylene, —O—($C_{2-4}$ alkylene), —O—($C_{1-4}$ alkylene)-O—, —(O)C—CH=CH— or —CH=CH—C(O)— or when Z is $CR^4$, —$OR^3$ and $R^4$ are joined to form —O—($C_{2-5}$ alkylene)- or —O—($C_{1-5}$ alkylene)-O— wherein each alkyl, alkylene, alkenyl, alkynyl and cycloalkyl group is optionally substituted with 1 to 5 fluoro substituents;
each $R^5$ and $R^7$ is independently selected from the group consisting of $C_{3-5}$ cycloalkyl, $C_{6-10}$ aryl, —C(O)($C_{6-10}$ aryl), $C_{2-9}$ heteroaryl, —C(O)($C_{2-9}$ heteroaryl) and $C_{3-6}$ heterocyclic wherein the cycloalkyl group is optionally substituted with 1 to 5 fluoro substituents and the aryl, heteroaryl and heterocyclic groups are optionally substituted with 1 to 3 substituents independently selected from $R^k$ and the aryl and heteroaryl groups are optionally further substituted with a phenyl group, where the phenyl group is optionally substituted with 1 to 3 substituents independently selected from $R^k$;
each $R^6$ and $R^8$ is independently selected from the group consisting of —OH, —$OR^9$, —$SR^9$, —$S(O)R^9$, —$S(O)_2R^9$, —$C(O)R^9$, $C_{3-5}$ cycloalkyl, $C_{6-10}$ aryl, $C_{2-9}$ heteroaryl and $C_{3-6}$ heterocyclic wherein the cycloalkyl group is optionally substituted with 1 to 5 fluoro substituents; and the aryl, heteroaryl and heterocyclic groups are optionally substituted with 1 to 3 substituents independently selected from $R^k$;
each $R^9$ is independently selected from the group consisting of $C_{1-4}$ alkyl, $C_{3-5}$ cycloalkyl, $C_{6-10}$ aryl and $C_{2-9}$ heteroaryl wherein the alkyl and cycloalkyl groups are optionally substituted with 1 to 5 fluoro substituents; and the aryl and heteroaryl groups are optionally substituted with 1 to 3 substituents independently selected from $R^k$;
$R^{10}$ and $R^{11}$ are independently $C_{1-6}$ alkyl or $R^{10}$ and $R^{11}$ are joined to form $C_{2-6}$ alkylene;
each $R^d$ is independently selected from the group consisting of $C_{1-4}$ alkyl and fluoro wherein each alkyl group is optionally substituted with 1 to 5 fluoro substituents;
each $R^f$ is independently selected from the group consisting of hydrogen, $C_{1-4}$ alkyl, $C_{2-4}$ alkenyl, $C_{2-4}$ alkynyl and $C_{3-6}$ cycloalkyl wherein each alkyl, alkenyl, alkynyl and cycloalkyl group is optionally substituted with 1 to 5 fluoro substituents;
each $R^g$ and $R^h$ is independently selected from the group consisting of hydrogen, $C_{1-4}$ alkyl, $C_{2-4}$ alkenyl, $C_{2-4}$ alkynyl and $C_{3-6}$ cycloalkyl or $R^g$ and $R^h$ are joined together with the nitrogen atom to which they are attached to form $C_{3-6}$ heterocyclic; wherein each alkyl, alkenyl, alkynyl and cycloalkyl group is optionally substituted with 1 to 5 fluoro substituents, and the heterocyclic group is optionally substituted with 1 to 3 substituents independently selected from $C_{1-4}$ alkyl and fluoro;
each $R^k$ is independently selected from the group consisting of $C_{1-4}$ alkyl, $C_{2-4}$ alkenyl, $C_{2-4}$ alkynyl, cyano, halo, —$OR^f$, —$SR^f$, —$S(O)R^f$, —$S(O)_2R^f$ and —$NR^gR^h$ or two adjacent $R^k$ groups are joined to form $C_{3-6}$ alkylene, —($C_{2-4}$ alkylene)—O— or —O—($C_{1-4}$ alkylene)-O— wherein each alkyl, alkylene, alkenyl and alkynyl group is optionally substituted with 1 to 5 fluoro substituents;
each —$CH_2$— group in a compound of Formula (I) is optionally substituted with one or two substituents independently selected from the group consisting of $C_{1-2}$ alkyl, and fluoro where each alkyl group is optionally substituted with 1 to 3 fluoro groups;
a is an integer from 2 to 7;
b is 0 or 1;
c is an integer from 2 to 7; provided that a+b+c equals 7, 8 or 9;

r is an integer from 0 to 4;
x is an integer from 2 to 4; and
y is an integer from 2 to 4;
wherein each heterocyclic group is independently selected from a pyrrolidine, imidazolidine, pyrazolidine, piperidine, 1,4-dioxane, morpholine, thiomorpholine, piperazine, and 3-pyrroline group; and
wherein each heteroaryl group is independently selected from a pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, and quinoxaline group.

36. The compound of claim 35, wherein b and r are 0.
37. The compound of claim 35, wherein $R^2$ is $C_{1-4}$ alkyl.
38. The compound of claim 35, wherein $R^2$ is isopropyl.
39. The compound of claim 35, wherein $R^3$ is $C_{1-4}$ alkyl.
40. The compound of claim 35, wherein $R^3$ is methyl.
41. The compound of claim 35, wherein W, Y and Z are CH and X is N.
42. The compound of claim 35, wherein $R^2$ is $C_{1-4}$ alkyl, $R^3$ is $C_{1-4}$ alkyl, b and r are 0, W, Y and Z are CH and X is N.
43. The compound of claim 35, wherein $R^{10}$ and $R^{11}$ are selected independently from $C_{1-3}$ alkyl or $R^{10}$ and $R^{11}$ are joined to form $C_{2-4}$ alkylene.
44. The compound of claim 35, wherein $R^{10}$ and $R^{11}$ are both methyl.
45. A compound of Formula (X):

or a salt thereof wherein
$R^{10}$ and $R^{11}$ are independently $C_{1-6}$ alkyl; or $R^{10}$ and $R^{11}$ are joined to form $C_{2-6}$ alkylene.
46. The compound of claim 45, wherein $R^{10}$ and $R^{11}$ are both methyl.

* * * * *

UNITED STATES PATENT AND TRADEMARK OFFICE
CERTIFICATE OF CORRECTION

PATENT NO. : 7,572,918 B2 Page 1 of 1
APPLICATION NO. : 11/259833
DATED : August 11, 2009
INVENTOR(S) : Peterson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 919 days.

Signed and Sealed this

Seventh Day of September, 2010

David J. Kappos
*Director of the United States Patent and Trademark Office*